(12) United States Patent
Taylor et al.

(10) Patent No.: US 6,431,476 B1
(45) Date of Patent: Aug. 13, 2002

(54) APPARATUS AND METHOD FOR RAPID ULTRASONIC DISRUPTION OF CELLS OR VIRUSES

(75) Inventors: Michael T. Taylor, Newark; Phillip Belgrader, Manteca; Farzad Pourahmadi, Fremont; William A. McMillan, Cupertino; Ronald Chang, Redwood City; Douglas B. Dority, Mill Valley, all of CA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 09/469,724

(22) Filed: Dec. 21, 1999

(51) Int. Cl.[7] .............................................. B02C 19/00
(52) U.S. Cl. ................................ 241/1; 241/2; 241/301
(58) Field of Search ................................. 241/1, 2, 301, 241/172; 435/306.1, 259

(56) References Cited

U.S. PATENT DOCUMENTS

| 3,799,742 A | 3/1974 | Coleman ................... 23/253 R |
| 4,426,451 A | 1/1984 | Columbus ................... 436/518 |

(List continued on next page.)

FOREIGN PATENT DOCUMENTS

| DE | 19519015 | 9/1996 |
| EP | 0 271 448 | 6/1988 |
| EP | 0 337 690 | 10/1989 |
| EP | 0 430 248 A2 | 6/1991 |
| EP | 0 576 602 B1 | 11/1995 |
| GB | 938163 | 10/1963 |
| WO | WO 92/05442 | 4/1994 |
| WO | WO 95/12808 | 5/1995 |
| WO | WO 96/07954 | 3/1996 |
| WO | WO 96/12541 | 5/1996 |
| WO | WO 97/02357 | 1/1997 |
| WO | WO 98/08594 | 3/1998 |
| WO | WO 98/10277 | 3/1998 |
| WO | WO 98/38487 | 9/1998 |
| WO | 0 123 456 A2 | 1/2000 |

OTHER PUBLICATIONS

US 5,693,782, 12/1997, Woodard et al. (withdrawn)
Anderson et al., "Microfluidic Biochemical Analysis System", *Transducers '97, Int'l Conf. on Solid0State Sensors and Actuators,* Chicago, Jun. 16–19, (1997), p. 477–480.
Brody et al., "Deformation and Flow of Red Blood Cells in a Synthetic Lattice: Evidence for an Active Cytoskeleton", *Biophysical Journal* : 68:2224–2232 (1995).
Brody et al., "Diffusion–Based Extraction in a Microfabricated Device", *Sensors and Actuators A* 58:13–18 (1997).
Branebjerg et al., "Fast Mixing by Lamination", Proceedings of the Conference on MEMS, Feb. 11–15, 1996, San Diego, CA.

(List continued on next page.)

*Primary Examiner*—Mark Rosenbaum
(74) *Attorney, Agent, or Firm*—Townsend and Townsend and Crew LLP

(57) ABSTRACT

The present invention provides an apparatus and method for disrupting cells or viruses to release the nucleic acid therefrom. The apparatus includes a container having a chamber for holding the cells or viruses. The apparatus also includes an ultrasonic transducer for contacting a wall of the chamber and for transmitting ultrasonic energy into the chamber through the wall. A support structure holds the container and the transducer against each other such that the transducer contacts the wall of the chamber. The support structure includes an elastic body, such as a spring, for applying to the container or to the transducer a substantially constant force to press together the transducer and the wall. The chamber also preferably contains beads for enhancing the disruption of the cells or viruses. The apparatus performs rapid and consistent lysis of cells or viruses, often in as little time as 5 to 10 seconds.

67 Claims, 14 Drawing Sheets

U.S. PATENT DOCUMENTS

| | | | |
|---|---|---|---|
| 4,642,220 A | 2/1987 | Björkman | 422/101 |
| 4,789,628 A | 12/1988 | Nayak | 435/7 |
| 4,855,240 A | 8/1989 | Rosenstein et al. | 436/514 |
| 4,874,137 A | * 10/1989 | Chiba | 241/2 |
| 4,891,120 A | 1/1990 | Sethi et al. | 204/600 |
| 4,895,500 A | 1/1990 | Hok et al. | 417/566 |
| 4,908,112 A | 3/1990 | Pace | 204/299 |
| 4,908,318 A | 3/1990 | Lerner | 435/270 |
| 4,915,812 A | 4/1990 | Parce et al. | 204/403 |
| 4,918,025 A | 4/1990 | Greener | 436/165 |
| 4,921,952 A | 5/1990 | Longmire et al. | 536/27 |
| 4,923,978 A | 5/1990 | McCormick et al. | 536/27 |
| 4,963,498 A | 10/1990 | Hillman et al. | 436/69 |
| 4,983,523 A | 1/1991 | Li et al. | 435/173 |
| 5,061,446 A | 10/1991 | Guigan | 422/64 |
| 5,074,474 A | * 12/1991 | Golz et al. | 241/1 |
| 5,114,858 A | 5/1992 | Williams et al. | 435/270 |
| 5,124,444 A | 6/1992 | Van Ness et al. | 536/27 |
| 5,155,018 A | 10/1992 | Gillespie et al. | 435/91 |
| 5,207,988 A | 5/1993 | Lucas | 422/73 |
| 5,223,219 A | 6/1993 | Subramanian et al. | 422/55 |
| 5,229,297 A | 7/1993 | Schnipelsky et al. | 436/94 |
| 5,234,809 A | 8/1993 | Boom et al. | 435/91 |
| 5,296,375 A | 3/1994 | Kricka et al. | 435/291 |
| 5,304,487 A | 4/1994 | Wilding et al. | 435/291 |
| 5,330,916 A | 7/1994 | Williams et al. | 435/311 |
| 5,342,931 A | 8/1994 | Woodard et al. | 436/25.4 |
| 5,351,777 A | 10/1994 | Jhingan | 536/25.4 |
| 5,374,522 A | 12/1994 | Murphy et al. | 435/6 |
| 5,374,533 A | 12/1994 | Murphy et al. | 435/6 |
| 5,422,241 A | 6/1995 | Goldrick et al. | 435/6 |
| 5,427,663 A | 6/1995 | Austin et al. | 204/180.1 |
| 5,427,946 A | 6/1995 | Kricka et al. | 435/291 |
| 5,438,129 A | 8/1995 | Woodard et al. | 536/25.4 |
| 5,443,590 A | 8/1995 | Öhman | 428/167 |
| 5,458,761 A | 10/1995 | Kamahori et al. | 204/602 |
| 5,500,071 A | 3/1996 | Kaltenbach et al. | 422/70 |
| 5,534,054 A | 7/1996 | Woodard et al. | 106/287.11 |
| 5,543,305 A | 8/1996 | Cummins et al. | 435/91.1 |
| 5,580,435 A | 12/1996 | Kovacs | 204/603 |
| 5,580,794 A | 12/1996 | Allen | 436/169 |
| 5,585,069 A | 12/1996 | Zanzucchi et al. | 422/100 |
| 5,587,128 A | 12/1996 | Wilding et al. | 422/50 |
| 5,605,662 A | 2/1997 | Heller et al. | 422/68.1 |
| 5,616,701 A | 4/1997 | Woodard et al. | 536/25.4 |
| 5,639,423 A | 6/1997 | Northrup et al. | 122/50 |
| 5,639,428 A | 6/1997 | Cottingham | 422/112 |
| 5,641,400 A | 6/1997 | Kaltenbach et al. | 204/451 |
| 5,652,141 A | 7/1997 | Henco et al. | 435/270 |
| 5,705,018 A | 1/1998 | Hartley | 156/345 |
| 5,707,799 A | 1/1998 | Hansmann et al. | 435/6 |
| 5,716,852 A | 2/1998 | Yager et al. | 436/172 |
| 5,741,639 A | 4/1998 | Ensing et al. | 204/452 |
| 5,842,787 A | 12/1998 | Kopf-Sill et al. | 366/340 |
| 5,843,767 A | 12/1998 | Beattie | 435/287.1 |
| 5,846,727 A | 12/1998 | Soper et al. | 204/451 |
| 5,856,174 A | 1/1999 | Lipshutz et al. | 422/68.1 |
| 5,858,188 A | 1/1999 | Soane et al. | 204/450 |
| 5,863,502 A | 1/1999 | Southgate et al. | 422/58 |
| 5,863,801 A | 1/1999 | Southgate et al. | 422/68.1 |
| 5,869,004 A | 2/1999 | Parce et al. | 422/100 |
| 5,874,046 A | 2/1999 | Megerie | 422/68.1 |
| 5,880,071 A | 3/1999 | Parce et al. | 204/453 |
| 5,921,678 A | 7/1999 | Desai et al. | 366/336 |
| 5,972,710 A | 10/1999 | Weigl et al. | 436/34 |
| 6,168,948 B1 | 1/2000 | Anderson et al. | 435/287.2 |
| 6,042,709 A | 3/2000 | Parce et al. | 204/453 |
| 6,068,752 A | 5/2000 | Dubrow et al. | 204/604 |
| 6,080,295 A | 6/2000 | Parce et al. | 204/451 |
| 6,090,545 A | 7/2000 | Wohlstadter et al. | 435/6 |
| 6,100,084 A | 8/2000 | Miles et al. | 435/306.1 |
| 6,153,073 A | 11/2000 | Dubrow et al. | 204/453 |
| 6,156,273 A | 12/2000 | Regnier et al. | 422/70 |

OTHER PUBLICATIONS

Buck, George E. et al., Rapid, Simple Method for Treating Clinical Specimens Containing *Mycobacterium tuberculosis* To Remove DNA for Polymerase Chain Reaction Journal of Clinical Microbiology, May 1992, p.1331–1334.

Cuypers et al., "The NucliSens™ Extractor for Automated Nucleic Acid Isolation", *Infusionsther Transfusionsmed*, 1998;25:147–151.

Klaassen et al., "Silicon Fusion Bonding and Deep Reactive Ion Etching: A New Technology for Microstructures", *Sensors and Actuators A* 52:132–139 (1996).

Maluf, N., "Silicon Fusion Bonding Plus DRIE Delivers Design Flexibility", *Micromachine Devices* 2:4–5 (1997).

Sanz B. et al., Effect of Ultrasonic Waves on the Heat Resistance Of *Bacillus Stearothermophilus* Spores Fundamental And Applied Aspects of Bacterial Spores, 1985, pp. 251–259.

* cited by examiner

APPARATUS AND METHOD FOR RAPID ULTRASONIC DISRUPTION OF CELLS OR VIRUSES

FIELD OF THE INVENTION

The present invention relates to an apparatus and method for rapidly disrupting cells or viruses using ultrasonic energy.

BACKGROUND OF THE INVENTION

The extraction of nucleic acid from cells or viruses is a necessary task for many applications in the fields of molecular biology and biomedical diagnostics. Once released from the cells, the nucleic acid may be used for genetic analysis, e.g., sequencing, pathogen identification and quantification, nucleic acid mutation analysis, genome analysis, gene expression studies, pharmacological monitoring, storing of DNA libraries for drug discovery, etc. The genetic analysis typically involves nucleic acid amplification and detection using known techniques. For example, known polynucleotide amplification reactions include polymerase chain reaction (PCR), ligase chain reaction (LCR), QB replicase amplification (QBR), self-sustained sequence replication (3SR), strand-displacement amplification (SDA), "branched chain" DNA amplification, ligation activated transcription (LAT), nucleic acid sequence-based amplification (NASBA), repair chain reaction (RCR), and cycling probe reaction (CPR).

The extraction of nucleic acids from cells or viruses is generally performed by physical or chemical methods. Chemical methods typically employ lysing agents. (e.g., detergents, enzymes, or strong organics) to disrupt the cells and release the nucleic acid, followed by treatment of the extract with chaotropic salts to denature any contaminating or potentially interfering proteins. Such chemical methods are described in U.S. Pat. No. 5,652,141 to Henco et al. and U.S. Pat. No. 5,856,174 to Lipshutz et al. One disadvantage to the use of harsh chemicals for disrupting cells is that the chemicals are inhibitory to subsequent amplification of the nucleic acid. In using chemical disruption methods, therefore, it is typically necessary to purify the nucleic acid released from the cells before proceeding with further analysis. Such purification steps are time consuming, expensive, and reduce the amount of nucleic acid recovered for analysis.

Physical methods for disrupting cells often do not require harsh chemicals that are inhibitory to nucleic acid amplification (e.g., PCR). These physical methods, however, also have their disadvantages. For example, one physical method for disrupting cells involves placing the cells in a solution and heating the solution to a boil to break open the cell walls. Unfortunately, the heat will often denature proteins and cause the proteins to stick to the released nucleic acid. The proteins then interfere with subsequent attempts to amplify the nucleic acid. Another physical method is freeze thawing in which the cells are repeatedly frozen and thawed until the cells walls are broken. Unfortunately, freeze thawing often fails to break open many structures, most notably certain spores and viruses that have extremely tough outer layers.

Another physical method for disrupting cells is the use of a pressure instrument. With this method, a solution of mycobacterial microorganisms is passed through a very small diameter hole under high pressure. During passage through the hole, the mycobacteria are broken open by the mechanical forces and their internal contents are spilled into solution. Such a system, however, is large, expensive and requires a cooling system to prevent excessive heat from building up and damaging the contents of the lysed cells. Moreover, the instrument needs to be cleaned and decontaminated between runs and a large containment system is required when infectious material is handled. A further disadvantage to this system is that the solution must contain only particles having substantially the same size, so that it may not be used to process many untreated clinical or biological specimens.

It is also known that cells can be lysed by subjecting the cells to ultrasonic agitation. This method is disclosed by Murphy et al. in U.S. Pat. No. 5,374,522. According to the method, solutions or suspensions of cells are placed in a container with small beads. The container is then placed in an ultrasound bath until the cells disrupt, releasing their cellular components. This method has several disadvantages. First, the distribution of ultrasonic energy in the bath is not uniform, so that a technician must locate a high energy area within the bath and place the container into that area. The non-uniform distribution of ultrasonic energy also produces inconsistent results. Second, the ultrasound bath does not focus energy into the container so that the disruption of the cells often takes several minutes to complete, a relatively long period of time when compared to the method of the present invention. Third, it is not practical to carry an ultrasound bath into the field for use in biowarfare detection, forensic analysis, or on-site testing of environmental samples.

SUMMARY

The present invention overcomes the disadvantages of the prior art by providing an improved apparatus and method for disrupting cells or viruses to release the nucleic acid therefrom. In contrast to the prior art methods described above, the present invention provides for the rapid and effective disruption of cells or viruses, including tough spores, without requiring the use of harsh chemicals. The disruption of the cells or viruses can often be completed in 5 to 10 seconds. In addition, the apparatus and method of the present invention provide for highly consistent and repeatable lysis of cells or viruses, so that consistent results are achieved from one use of the apparatus to the next.

The apparatus includes a container having a chamber for holding the cells or viruses. The container has at least one wall defining the chamber. The apparatus also includes an ultrasonic transducer, preferably an ultrasonic horn, for contacting an external surface of the wall and for transmitting ultrasonic energy into the chamber through the wall. The apparatus further includes a support structure for holding the container and the transducer against each other such that the transducer contacts the external surface of the wall and for applying to the container or to the transducer a substantially constant force to press together the transducer and the wall. In a preferred embodiment, the support structure comprises a base, a first holder attached to the base for holding the transducer, and a second holder for holding the container. The second holder is slidably mounted to the base for positioning the container against the transducer such that the external surface of the wall contacts the transducer. The support structure also includes at least one elastic body (e.g., a spring) for applying to the second holder the substantially constant force to press the wall against the transducer.

In operation, a liquid or gel containing the cells or viruses is held in the chamber of the container. Beads are also preferably placed in the chamber to enhance the disruption of the cells or viruses. The ultrasonic transducer is then held against the wall of the chamber, and the constant force is applied to the container or to the transducer to press together the transducer and the wall. Ultrasonic energy is then transmitted from the transducer into the chamber to disrupt the cells or viruses, releasing the nucleic acid therefrom. The apparatus and method are effective for rapidly and consistently lysing cells or viruses without the use of harsh chemicals that inhibit nucleic acid amplification.

DETAILED DESCRIPTION

The present invention provides an apparatus and method for disrupting cells or viruses. The cells may be animal or plant cells, spores, bacteria, or microorganisms. The viruses may be any type of infective agents having a protein coat surrounding an RNA or DNA core.

The apparatus includes a container having a chamber for holding the cells or viruses. The apparatus also includes an ultrasonic transducer, preferably an ultrasonic horn, for contacting a wall of the chamber and for transmitting ultrasonic energy into the chamber through the wall. The apparatus further includes a support structure for holding the container and the transducer against each other such that the transducer contacts the wall of the chamber and for applying a substantially constant force to the container or to the transducer to press together the transducer and the wall of the chamber. The transmission of ultrasonic energy from the transducer into the chamber rapidly disrupts the cells or viruses to release the nucleic acid therefrom.

Figure 1:
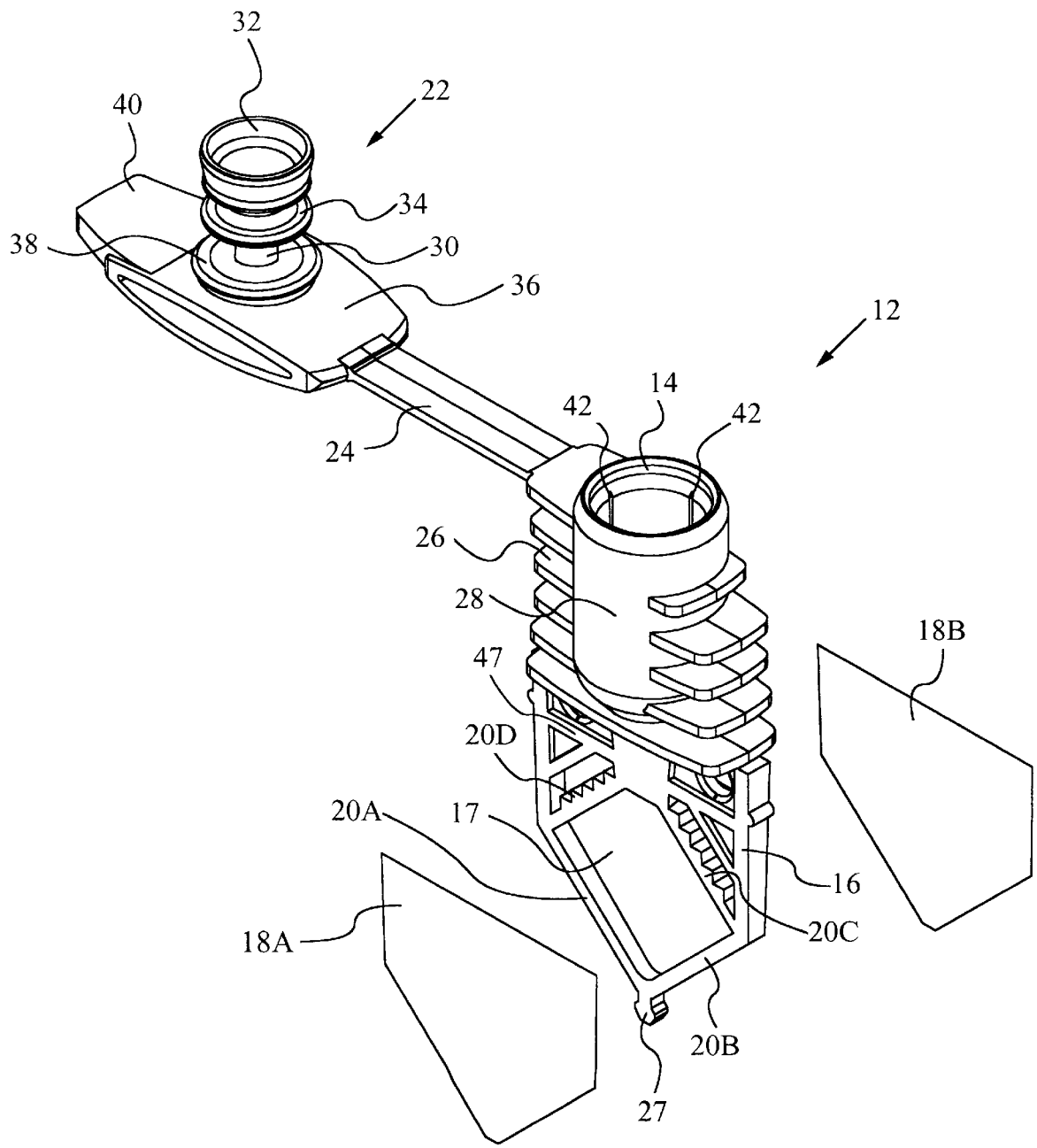
FIG. 1 is a partially exploded, isometric view of a container for holding cells or viruses to be disrupted according to a preferred embodiment of the invention.
Figure 2:
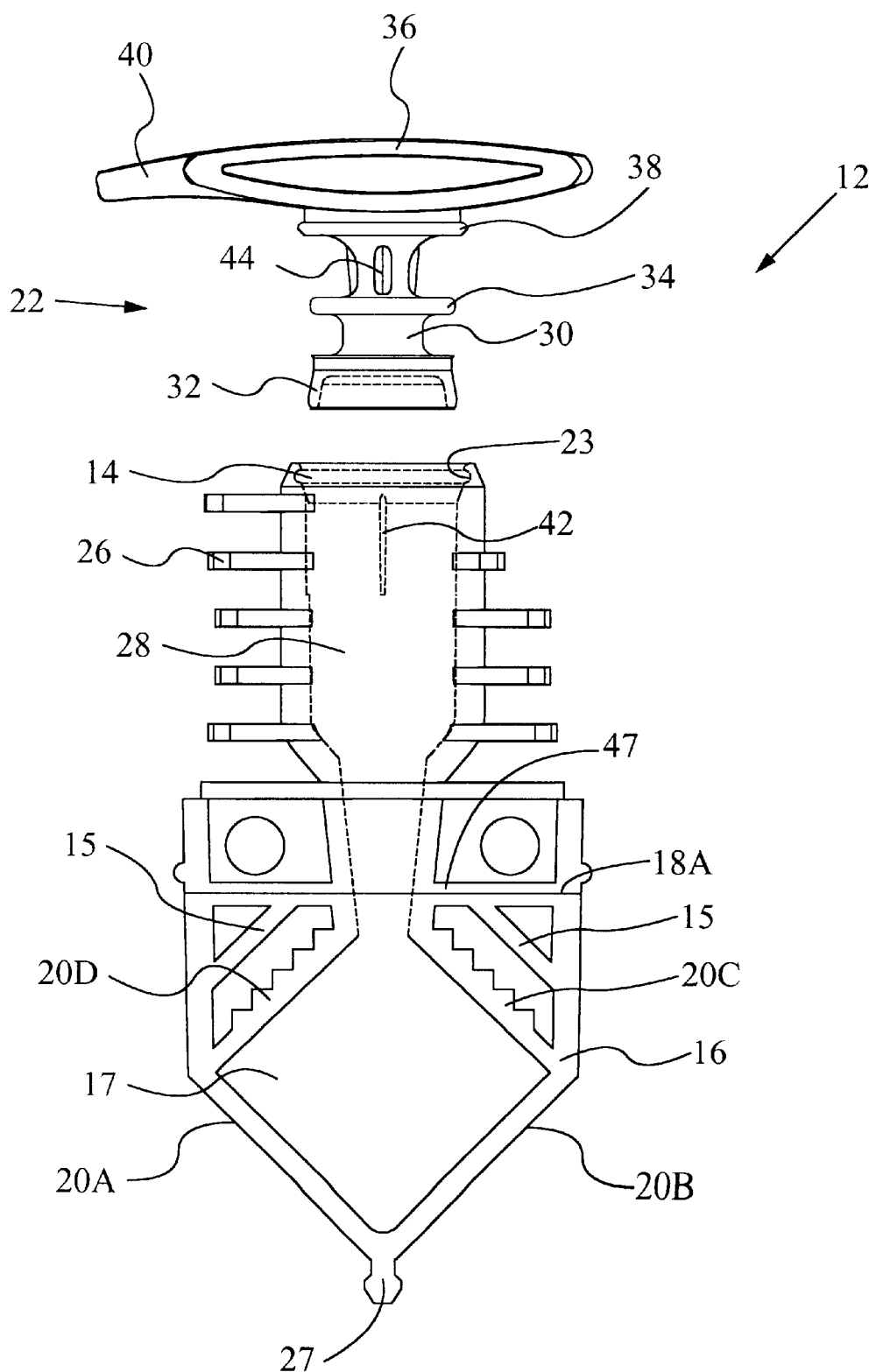
FIG. 2 is a schematic, front view of the container of FIG. 1.

FIGS. 1–12 show a preferred embodiment of the invention. FIG. 1 shows a partially exploded view of a container 12 for holding cells or viruses, and FIG. 2 shows a front view of the container 12. As shown in FIGS. 1–2, the container 12 has a chamber 17 for holding a liquid or gel containing cells or viruses to be disrupted. The container 12 has a rigid frame 16 that defines the side walls 20A, 20B, 20C, 20D of the chamber 17. The rigid frame. 16 also defines a port 14 and a channel 28 that connects the port 14 to the chamber 17. The container also includes thin, flexible sheets attached to opposite sides of the rigid frame 16 to form two spaced-apart, opposing major walls 18A, 18B of the chamber. The flexible major walls 18A, 18B are shown in FIG. 1 exploded from the rigid frame 16 for illustrative clarity. When the container is assembled, the major walls 18A, 18B are sealed to opposite sides of the frame 16, as is described in detail below. The chamber 17 is thus defined by the spaced apart, opposing major walls 18A, 18B and by the rigid side walls 20A, 20B, 20C, 20D that connect the major walls to each other.

The container 12 also includes a plunger 22 that is inserted into the channel 28 after adding the cells or viruses to the chamber 17. The plunger 22 compresses gas in the container 12 thereby increasing pressure in the chamber 17. The gas compressed by the plunger 22 is typically air filling the channel 28. The pressurization of the chamber 17 forces the flexible wall 18A to conform to the surface of the ultrasonic transducer (not shown in FIGS. 1–2), as is discussed in greater detail below. The plunger 22 also closes the port 14 and seals the chamber 17 from the environment external to the container.

In general, the plunger may comprise any device capable of establishing a seal with the walls of the channel 28 and of compressing gas in the container. Such devices include, but are not limited to, pistons, plugs, or stoppers. The plunger 22 of the preferred embodiment includes a stem 30 and a piston 32 on the stem. When the plunger 22 is inserted into the channel 28, the piston 32 establishes a seal with the inner walls of the channel and compresses air in the channel. The piston 32 is preferably a cup integrally formed (e.g., molded) with the stem 30. Alternatively, the piston 32 may be a separate elastomeric piece attached to the stem.

The plunger 22 also preferably includes an alignment ring 34 encircling the stem for maintaining the plunger 22 in coaxial alignment with the channel 28 as the plunger is inserted into the channel. The alignment ring 34 is preferably integrally formed (e.g., molded) with the stem 30. The stem 30 may optionally includes support ribs 44 for stiffening and strengthening the stem. The plunger 22 also includes a plunger cap 36 attached to the stem 30. As shown in FIG. 2, the cap 36 includes a snap ring 38 and the container includes an annular recess 23 encircling the port 14 for receiving the snap ring 38. The cap 36 may optionally include a lever portion 40 which is lifted to remove the plunger 22 from the channel 28. The container 12 may also include finger grips 26 for manual handling of the container.

Figure 7:
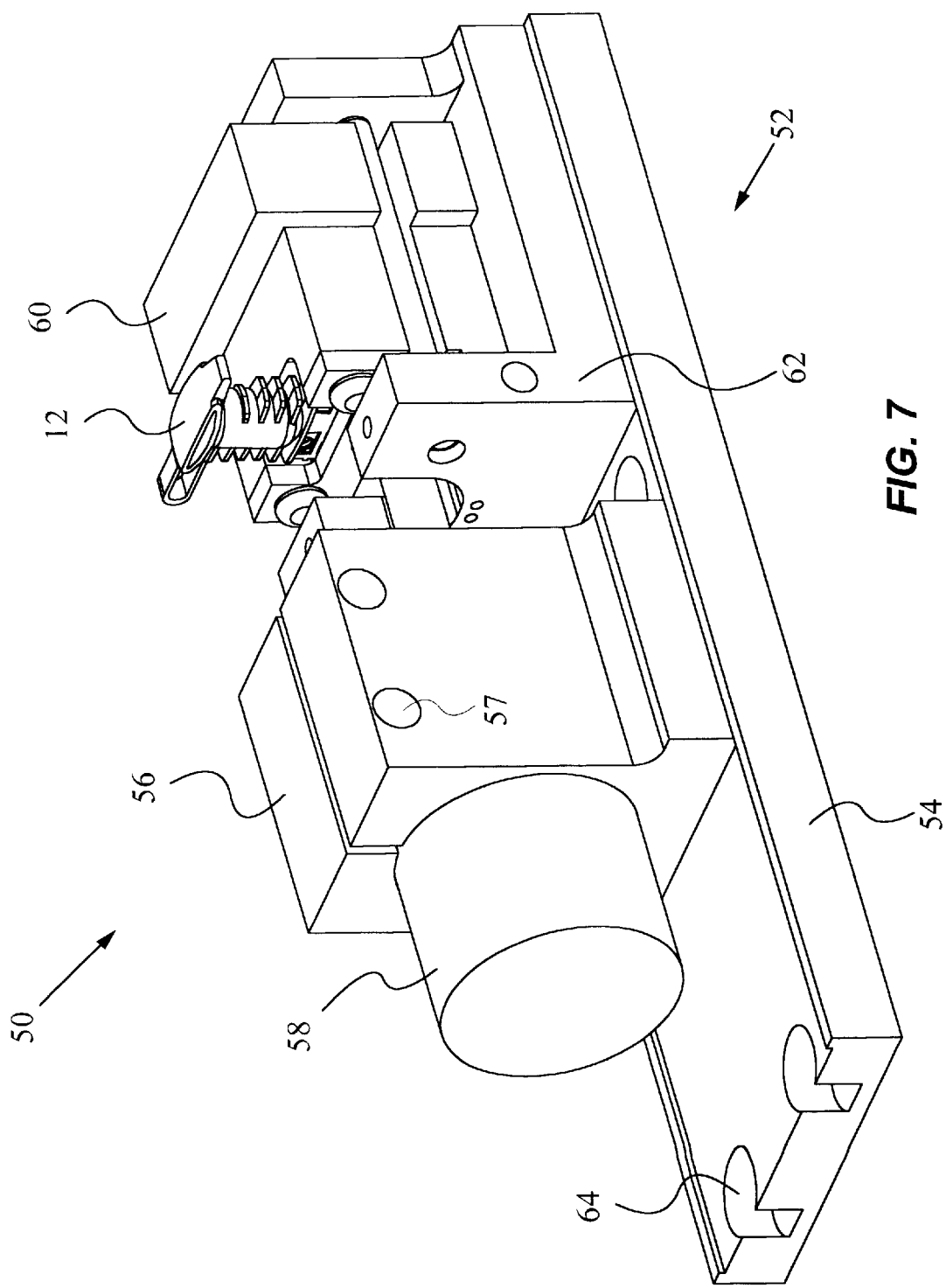
FIG. 7 is an isometric view of the container of FIG. 1 inserted into an apparatus for disrupting cells or viruses according to the preferred embodiment of the invention.

FIG. 7 shows an isometric view of an apparatus 50 for disrupting cells or viruses. The apparatus 50 includes, an ultrasonic transducer, preferably an ultrasonic horn 58, for transmitting ultrasonic energy into the chamber of the container 12. The apparatus 50 also includes a support structure 52 for holding the horn 58 and the container 12 against each other. The support structure 52 includes a base 54 and a first holder 56 attached to the base for holding the outer housing of the horn 58. The holder 56 includes a bore for receiving the horn 58 and screws or bolts 57 that are tightened to clamp the outer housing of the horn firmly in the holder. The base 54 may optionally include bolt holes 64 for bolting the support structure 52 to a surface, e.g., a counter or bench top.

Figure 8:
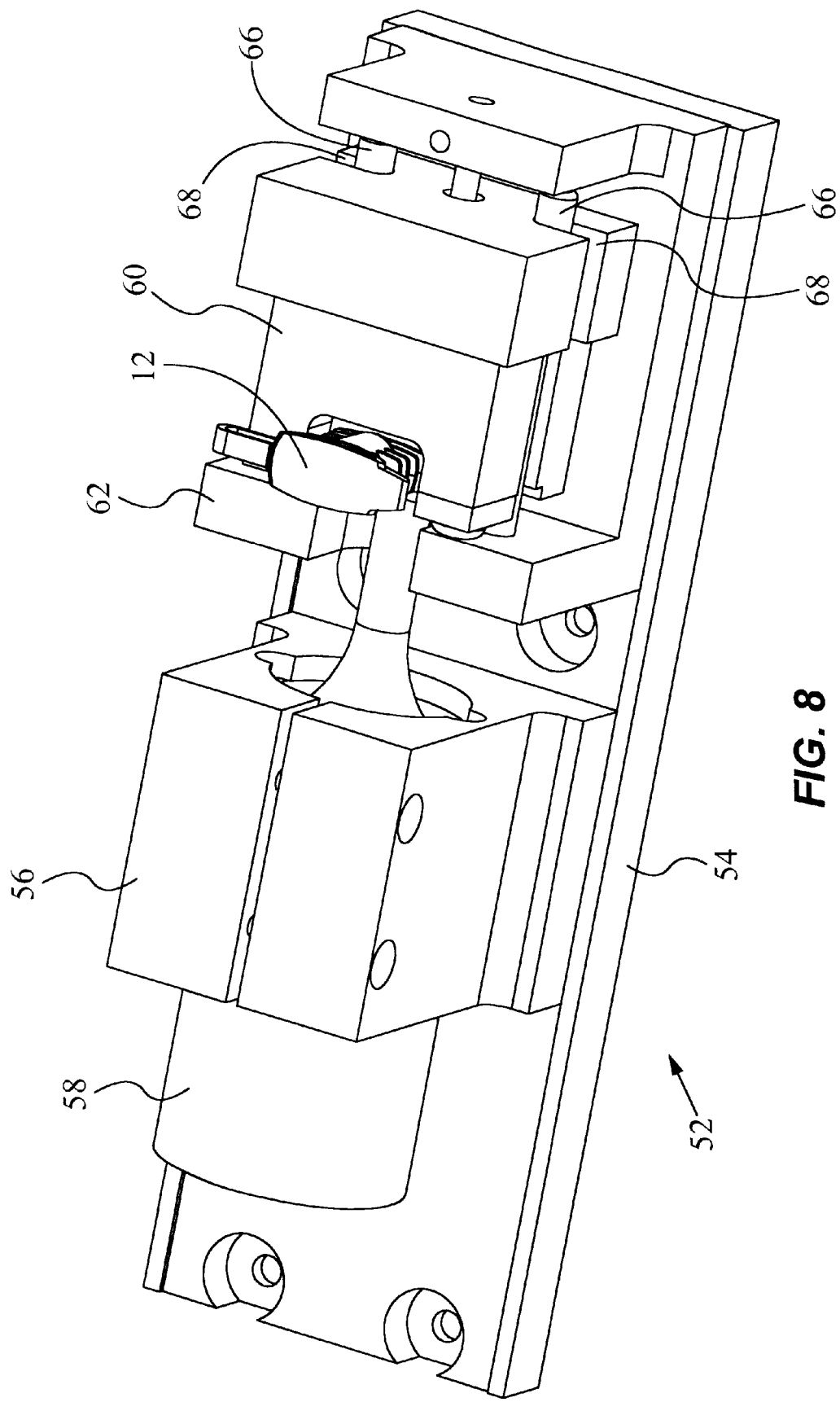
FIG. 8 is a different isometric view of the container of FIG. 1 inserted into the apparatus of FIG. 7.
Figure 9:
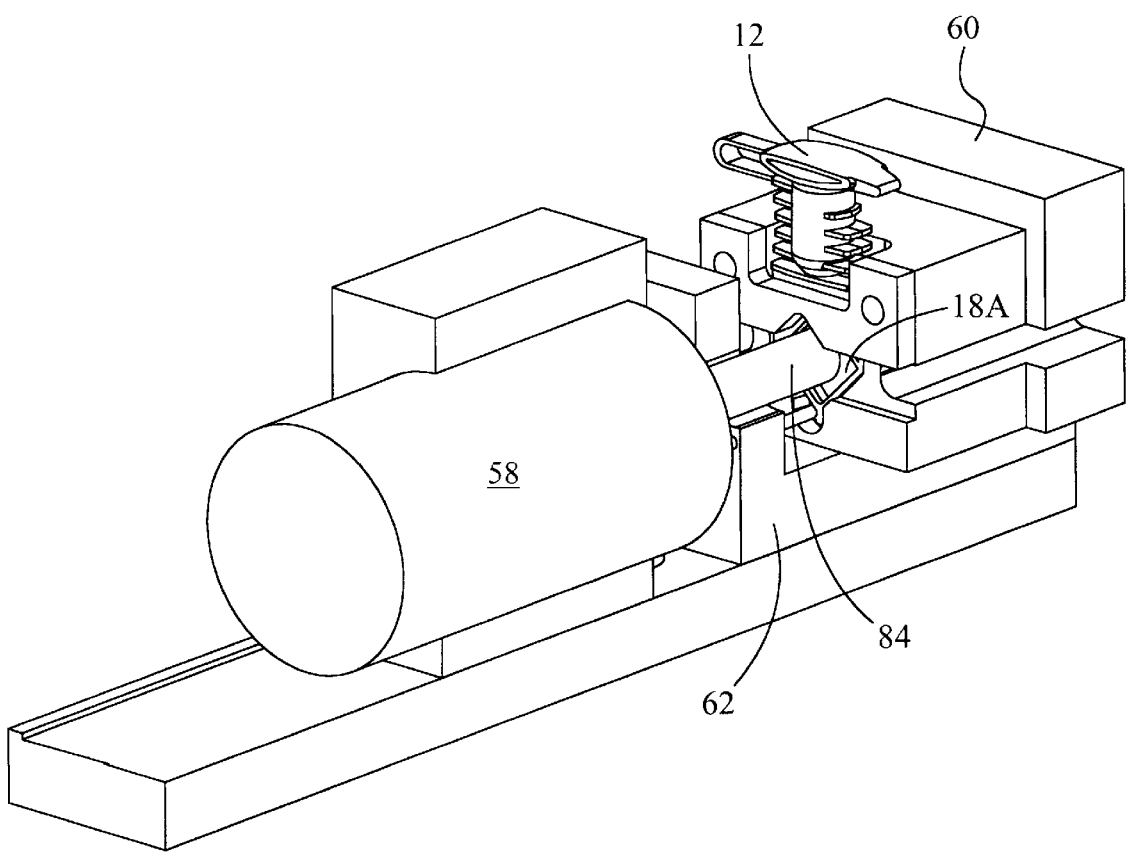
FIG. 9 is a partially cut-away, isometric view of the apparatus of FIG. 7.

As shown in FIG. 8, the support structure 52 also includes a holder 60 for holding the container 12. The holder 60 is slidably mounted to the base 54 by means of a guide 62. The guide 62 may be fixedly attached to the base 54 or integrally formed with the base. The guide 62 has two guide pins 66, and the holder 60 has two guide slots 68 for receiving the guide pins 66. The holder 60 may thus slide on the guide pins 66. As shown in the partially cut-away view of FIG. 9, the holder 60 is designed to hold the container 12 such that the external surface of the flexible wall 18A is exposed and accessible to the tip 84 of the ultrasonic horn 58. The guide 62 is appropriately aligned with the horn 58 to slide the holder 60 into a position in which the external surface of the flexible wall 18A contacts the horn tip 84.

Figure 10:
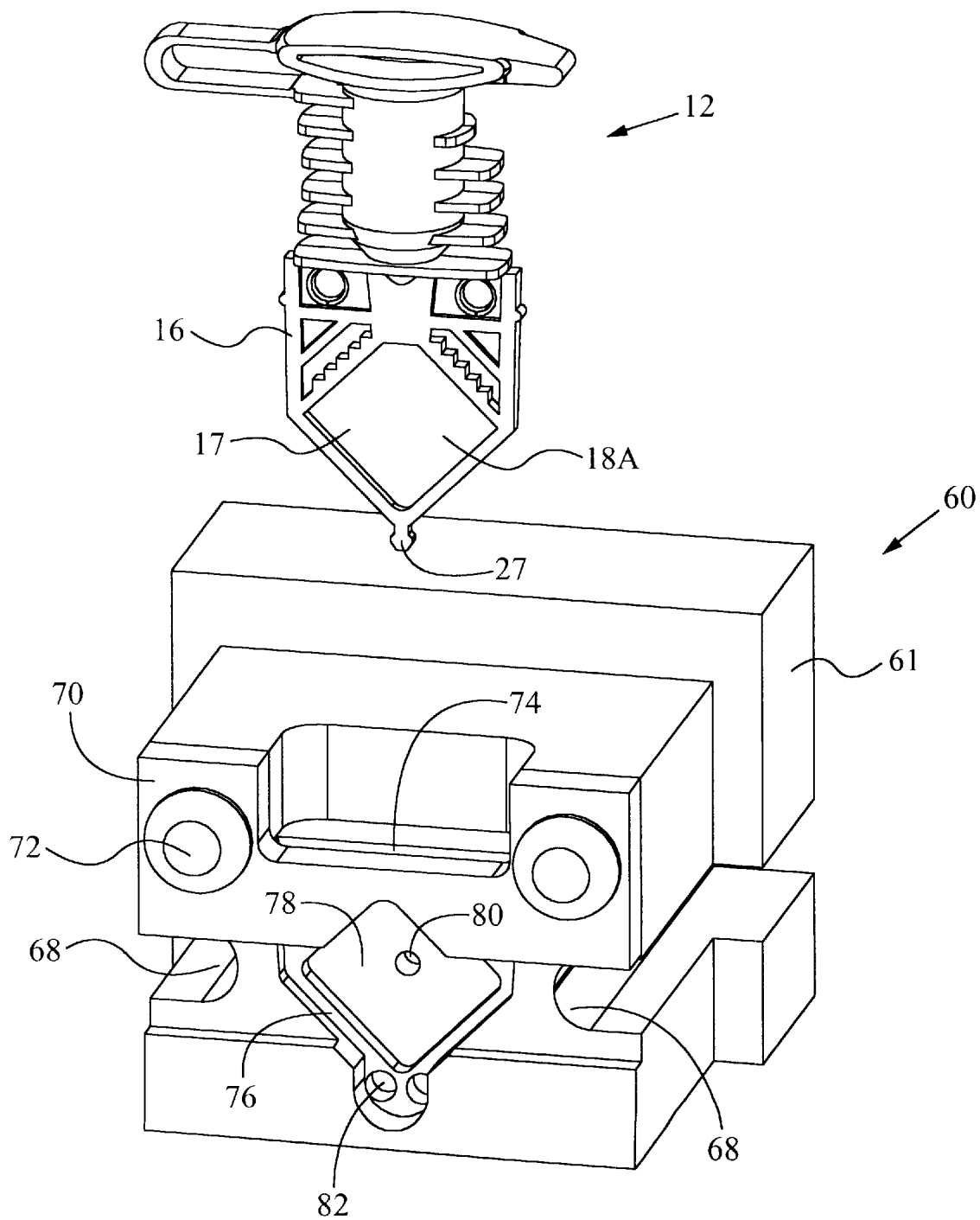
FIG. 10 is an isometric view of a holder for holding the container of FIG. 1.

FIG. 10 shows an isometric view of the holder 60. The holder 60 has a body 61 in which are formed the guide slots 68 for receiving the guide pins. The body also has a recess 76 for receiving the container 12. The shape of the recess 76 matches the shape of the lower portion of the frame 16 so that the frame fits securely in the recess 76. The holder 60 also includes a retaining member 70 attached to the body 61 by screws or bolts 72. The retaining member 70 and body 61 define a slot 74 through which the frame 16 is inserted when the frame is placed in the recess 76. The retaining member 70 holds the frame 16 in the recess. The body 61 also has an opening 78 adjacent the recess 76. The shape of the opening 78 corresponds to the shape of the chamber 17.

Figure 12:
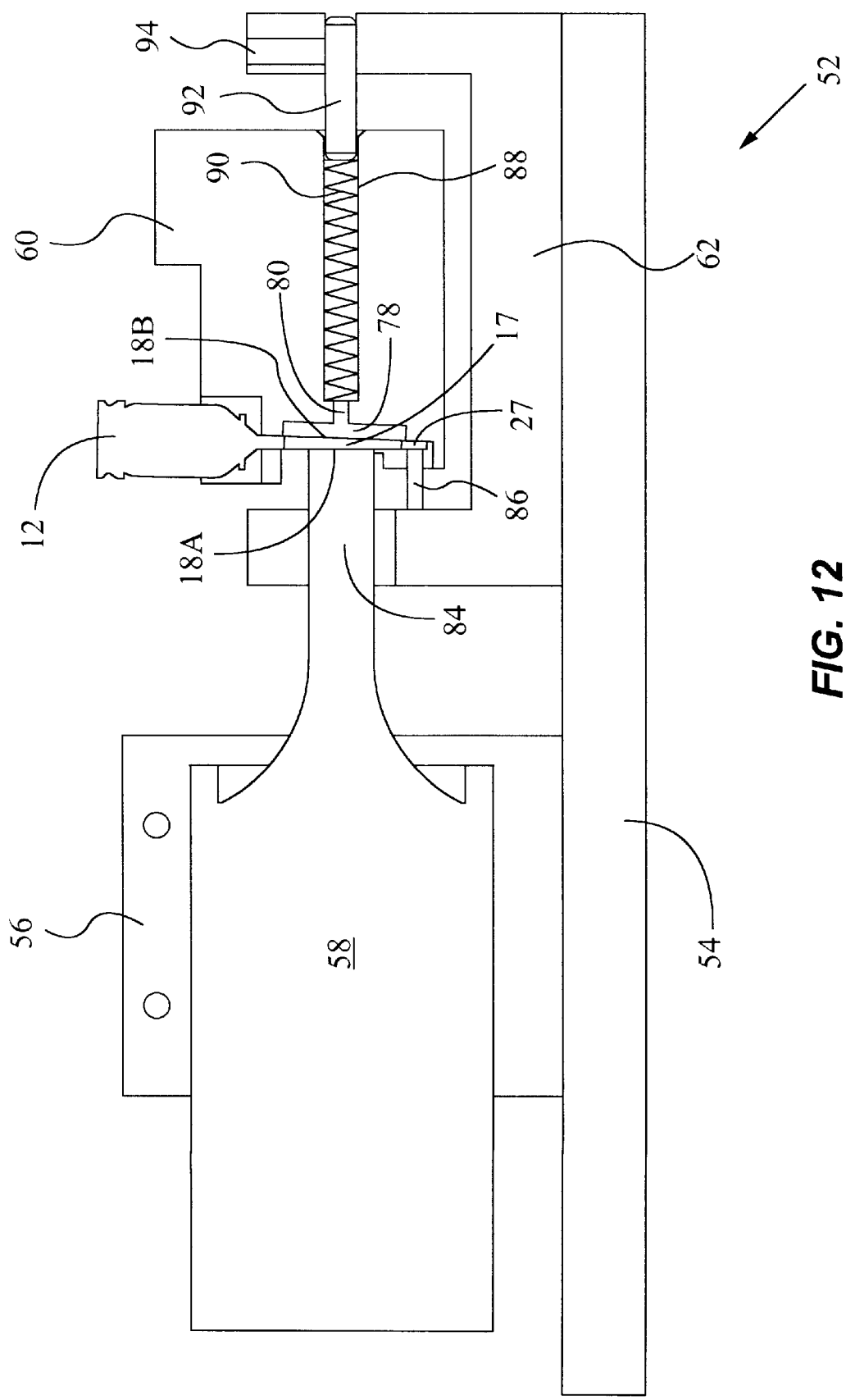
FIG. 12 is a schematic side view of the container of FIG. 1 inserted into the apparatus of FIG. 7 for disruption of the cells or viruses contained in the container.

As shown in the cross sectional view of FIG. 12, when the container 12 is inserted into the holder 60, the opening 78 is positioned next to the flexible wall 18B. The opening 78 is thus positioned to permit the flexible wall 18B to expand outwardly into the opening. The holder 60 holds only the frame of the container 12 so that the flexible walls 18A, 18B are unrestrained by the holder. The flexible wall 18A is therefore free to move inwardly and outwardly with the horn tip 84 as ultrasonic energy is transmitted from the tip 84 to the chamber 17. The flexible wall 18B is also free to move inwardly or outwardly as the ultrasonic energy is received in the chamber 17. This permits the liquid within the chamber 17 to move more freely as it receives the ultrasonic energy and thus enhances the ultrasonic action in the chamber 17. Venting of the opening 78 is provided by first and second bores 80, 88 formed in the body of the holder 60. One end of the narrower bore 80 is connected to the opening 78 and the other end is connected to the larger bore 88. The bore 88 extends through the body of the holder 60 to permit the escape of gas (e.g., air) from the opening 78. The venting prevents pressure from building in the opening 78 when the flexible wall 18B expands into the opening. Such pressure would restrict the motion of the wall 18B.

Figure 11:
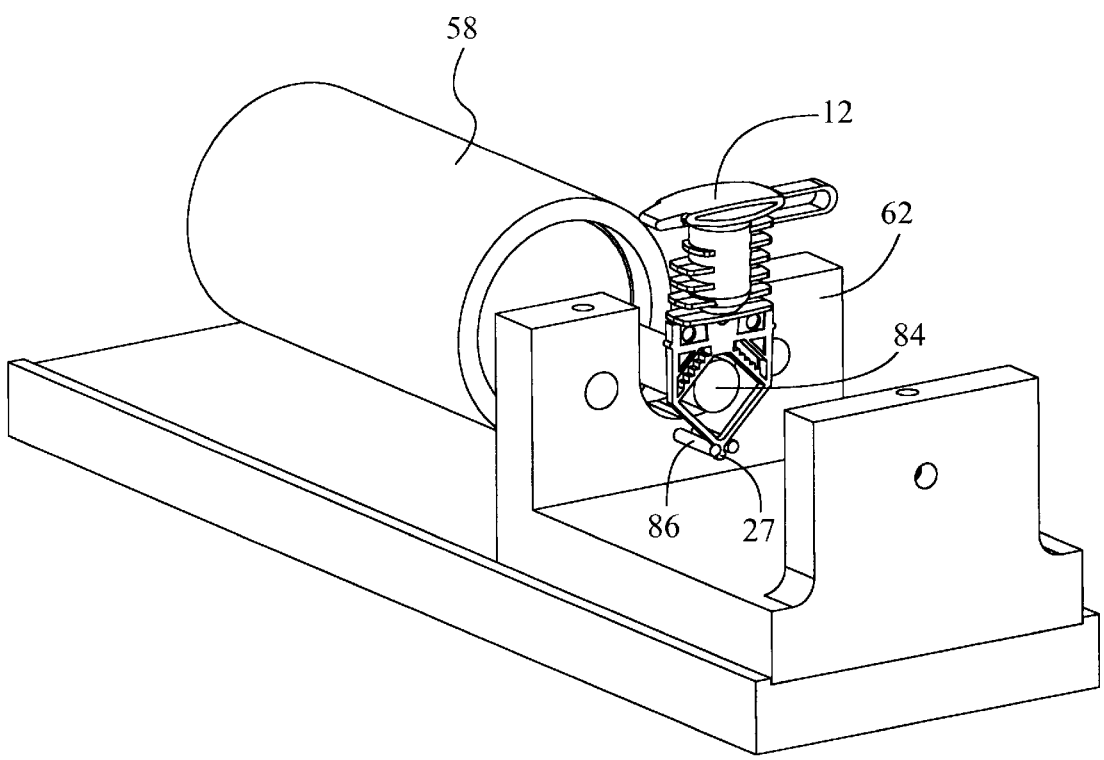
FIG. 11 is another isometric view of the apparatus of FIG. 7 in which several parts of the apparatus have been removed to show an ultrasonic horn contacting the container of FIG. 1.

Referring again to FIG. 10, the container 12 has a bulb-shaped tab 27 extending from the bottom of the frame 16. The holder 60 has holes 82 formed in the body 61 adjacent the recess 76. When the frame 16 is inserted into the recess 76, the tab 27 is positioned between the holes 82. The holes 82 are for receiving retaining pins. As shown in FIG. 11, the retaining pins 86 extend from the guide 62 (from which the guide pins have been removed for clarity in FIG. 11) and are positioned on opposite sides of the bulb-shaped tab 27 when the container 12 is moved into contact with the horn tip 84. The spacing of the pins 86 is less than the width of the bulb so that the pins 86 hold down the tab 27, and thus the container 12, as ultrasonic energy is transmitted into the container from the horn 58. This ensures that the container 12 does not rise out of position due to the motion of the horn tip 84. Alternatively, a collar or other suitable retention mechanism may be used to hold the container 12 in position.

Referring to FIG. 12, the support structure 52 also includes an elastic body, such as a spring 90, for applying a force to the holder 60 to press the wall 18A of the chamber 17 against the horn tip 84. When the wall 18A is in contact with the horn tip 84, the force provided by the spring is constant, providing for consistent coupling and transfer of power between the horn 58 and the container 12. The spring 90 is positioned in the bore 88. The holder 60 has an inner surface surrounding the junction of the larger bore 88 and the narrower bore 80. One end of the spring 90 contacts the inner surface, and the other end of the spring contacts a rod 92 that extends from the guide 62. The spring 90 is thus compressed between the surface of the holder 60 and the rod 92 so that it pushes the holder 60, and thus the flexible wall 18A of the container 12, against the horn tip 84.

The magnitude of the force provided by the spring 90 may be adjusted by changing the preload on the spring. The support structure 52 includes a rod 92 that contacts one end of the spring. The guide 62 includes a first bore for receiving the rod 92 and a second bore for receiving a set screw 94 that holds the rod 92 in a fixed position. To adjust the preload on the spring 90, the screw 94 is loosened, the rod 92 is moved to a new position, and the screw 94 is retightened to hold the rod 92 in the new position. The rod 92 and set screw 94 thus provide a simple mechanism for adjusting the preload on the spring 90. Once the preload on the spring 90 is adjusted to provide a suitable coupling force between the wall 18A and the horn tip 84, it is desirable to keep the preload constant from one use of the apparatus to the next so that valid comparisons can be made between different samples disrupted by the apparatus.

The flexible wall 18A facilitates the transfer of ultrasonic energy from the horn 58 into the chamber 17. The wall 18A is sufficiently flexible to conform to the surface of the horn tip 84, ensuring good coupling between the tip 84 and the wall 18A. The surface of the horn tip 84 that contacts the wall 18A is preferably planar (e.g., flat) to ensure power coupling over the entire area of the surface. Alternatively, the tip 84 may have a slightly curved (e.g., spherical) surface for contacting the wall 18A. The opposite wall 18B is preferably sufficiently flexible to move inwardly and outwardly as ultrasonic energy is received in the chamber 17. This permits the liquid within the chamber 17 greater freedom of movement as it receives the ultrasonic energy and thus enhances the ultrasonic action in the chamber 17. In alternative embodiments, the wall 18B may be rigid or restrained. The applicants have found, however, that when the wall 18B is rigid or restrained, more ultrasonic energy is required to disrupt the cells or viruses in the chamber 17.

Referring again to FIG. 1, the walls 18A, 18B are preferably flexible sheets or films of polymeric material such as polypropylene, polyethylene, polyester, or other polymers. The films may either be layered, e.g., laminates, or the films may be homogeneous. Layered films are preferred because they generally have better strength and structural integrity than homogeneous films. Alternatively, the walls 18A, 18B may comprise any other material that may be formed into a thin, flexible sheet. For good flexibility and energy transfer, the thickness of each wall is preferably in the range of 0.01 to 0.2 mm, and more preferably in the range of 0.025 to 0.1 mm. As previously described, the plunger 22 is inserted into the channel 28 after adding the cells or viruses to the chamber 17. The plunger 22 compresses air in the channel 28, thereby increasing pressure in the chamber 17. The pressurization of the chamber 17 forces the flexible wall 18A to conform to the surface of the horn tip, ensuring good coupling between the wall and the tip.

Figure 6A:
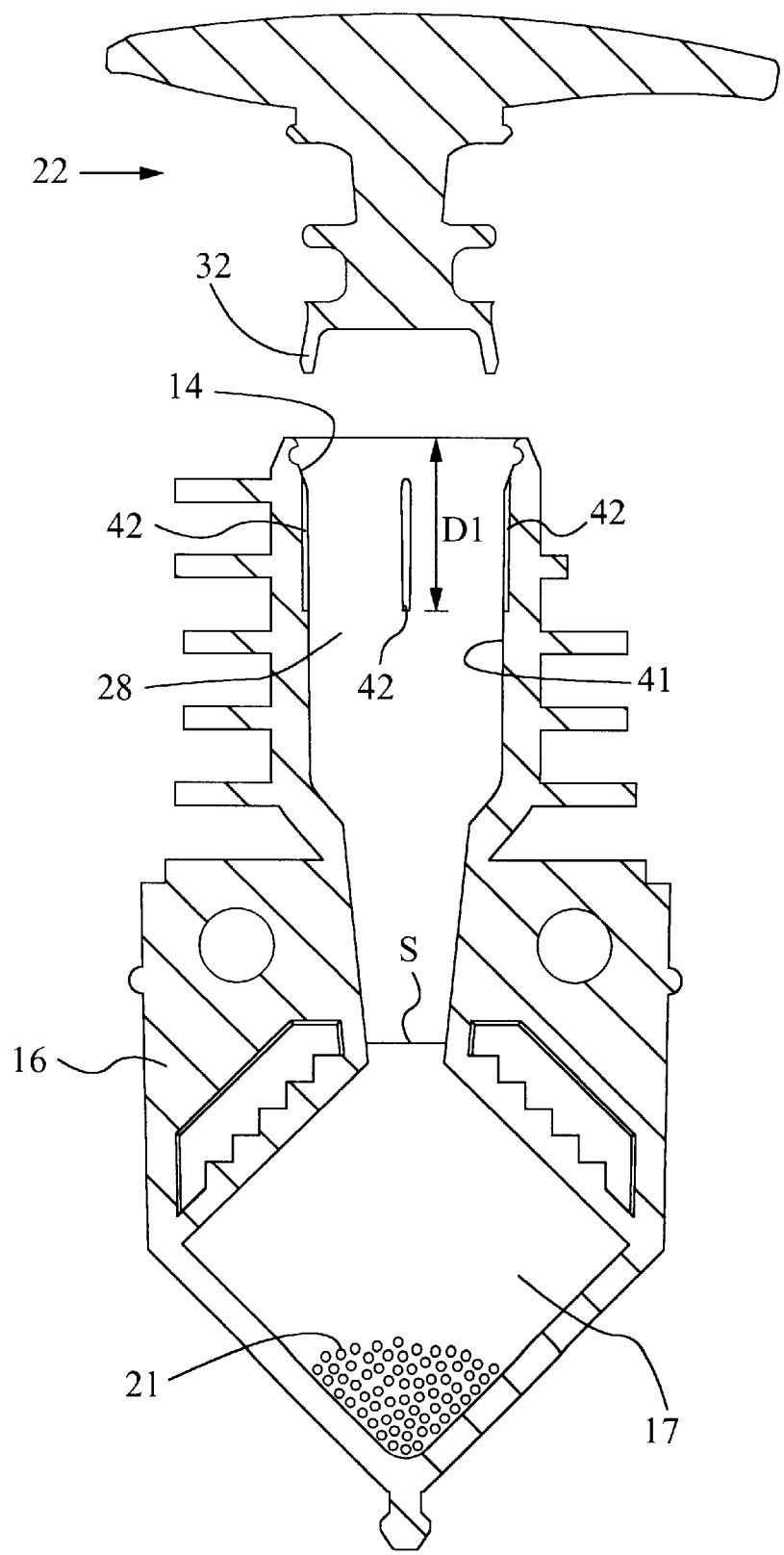
FIGS. 6A–6D are schematic, cross-sectional views of a plunger being inserted into a channel of the container of FIG. 1.

Referring to FIG. 6A, the rigid frame 16 has an inner surface 41 defining the channel 28. The inner surface 41 has one or more pressure control grooves 42 formed therein. Preferably, the inner surface has four pressure control grooves 42 (only three shown in the view of FIG. 6A) spaced equidistantly about the circumference of the channel 28. The grooves 42 extend from the port 14 to a predetermined depth $D_1$ in the channel 28. The grooves 42 allow gas to escape from the channel 28 and thus prevent pressurization of the chamber 17 until the piston 32 reaches the depth $D_1$ in the channel. When the piston 32 reaches the depth $D_1$, the piston establishes an annular seal with the walls of the channel 28 and begins to compress air trapped in the channel. The compression of the trapped air causes the desired pressurization of the chamber 17.

Figure 6B:
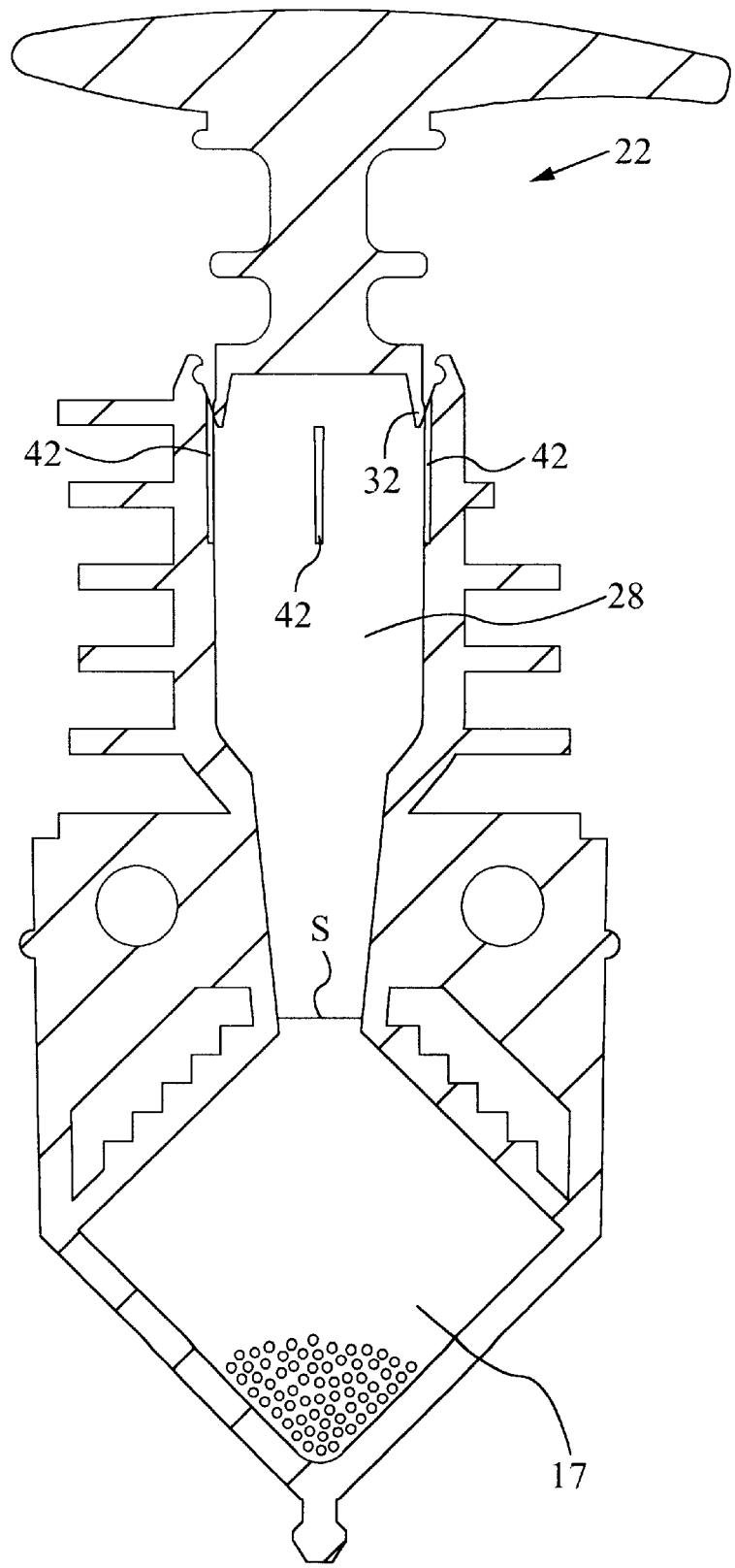

The stroke of the plunger 22 into the channel 28 is fully illustrated in FIGS. 6A–6D. As shown in FIG. 6A, prior to inserting the plunger 22 into the channel 28, the chamber 17 is filled with beads 21 and a liquid or gel containing the cells or viruses to be disrupted. Specific methods for filling the chamber are discussed below. The container 12 is filled to a surface level S. Also prior to inserting the plunger 22 into the channel 28, the channel 28 contains air having pressure equal to the pressure of the atmosphere external to the container, hereinafter called ambient pressure. The ambient pressure is usually standard atmospheric pressure, e.g., about 14.7 pounds per square inch (psi). As shown in FIG. 6B, when the plunger 22 is first inserted into the channel 28, the piston 32 begins to displace the air in the channel. The displaced air escapes from the channel 28 through the grooves 42.

Figure 6C:
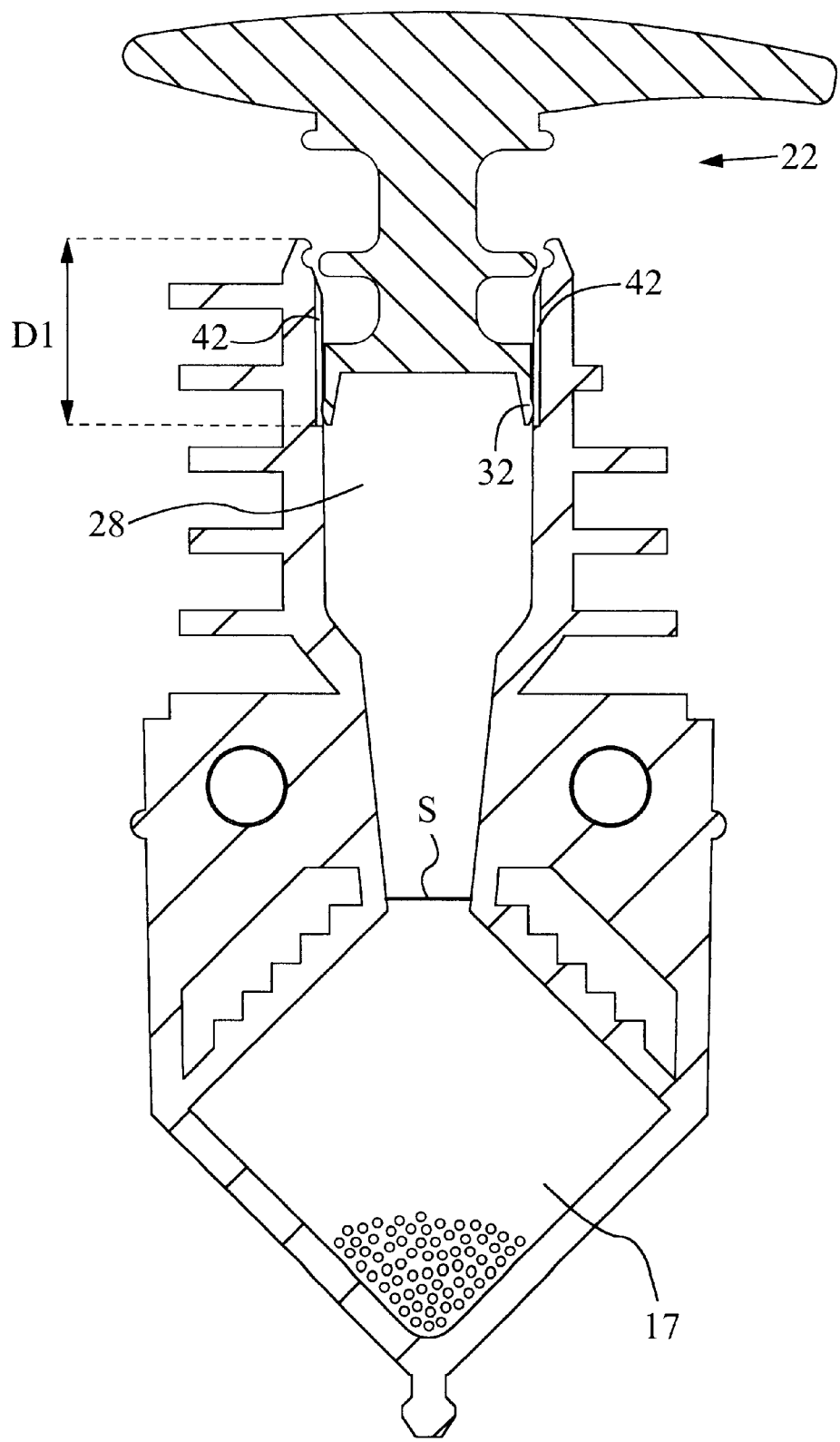
Figure 6D:
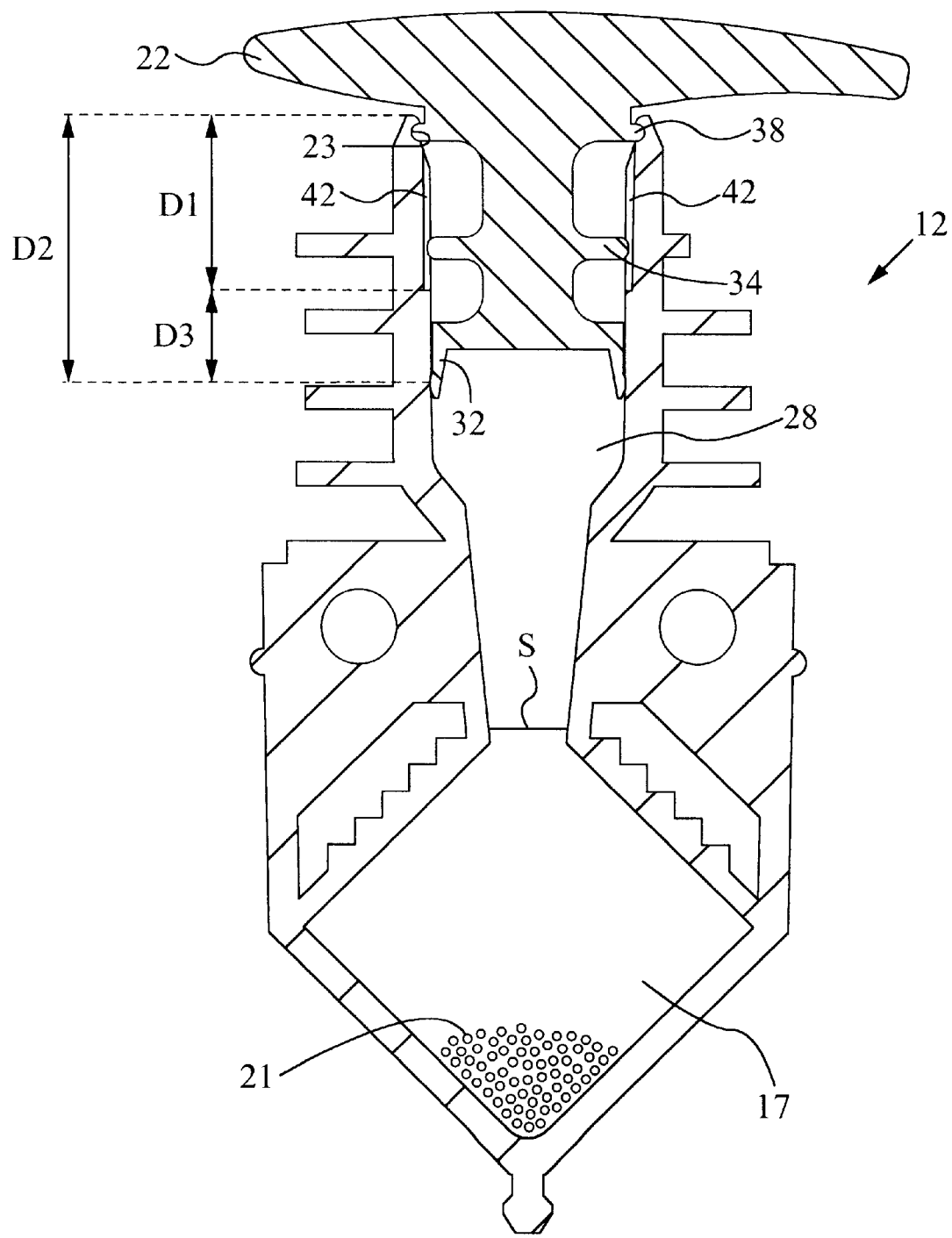

Referring now to FIG. 6C, when the piston 32 reaches the depth $D_1$ at which the pressure control grooves end, the piston 32 establishes an annular seal with the walls of the channel 28 and begins to compress air trapped in the channel between the piston 32 and the surface level S. As shown in FIG. 6D, as the plunger 22 is inserted further into the channel 28, the alignment ring 34 keeps the plunger 22 coaxially aligned with the channel 28 as the piston 32 continues to compress air trapped in the channel. When the plunger 22 is fully inserted in the channel 28, the snap ring 38 snaps into the annular recess 23, ending the plunger stroke.

When the plunger 22 is fully inserted, the piston 32 seals the channel 28 at a depth $D_2$ which is lower than the depth $D_1$ at which the pressure control grooves 42 terminate. The distance $D_3$ traveled by the piston 32 between depths $D_1$ and $D_2$, i.e. the distance of the pressure stroke, determines the amount of pressurization of the chamber 17. Referring again to FIG. 12, the pressure in the chamber 17 should be sufficiently high to ensure that the flexible wall 18A conforms to the surface of the horn tip 84. The pressure should not be so great, however, that the flexible wall 18A bursts or becomes unattached from the container 12.

It is presently preferred to pressurize the chamber 17 to a pressure in the range of 2 to 50 psi above ambient pressure. This range is presently preferred because 2 psi is generally enough pressure to ensure conformity between the flexible wall 18A and the horn tip 84, while pressures above 50 psi may cause bursting of the walls 18A, 18B or deformation of the frame of the container 12. More preferably, the chamber 17 is pressurized to a pressure in the range of 8 to 15 psi above ambient pressure. This range is more preferred because it is safely within the practical limits described above, i.e. pressures of 8 to 15 psi are usually more than enough to ensure conformity between the wall 18A and horn tip 84, but are lower than the pressures that might burst the walls 18A, 18B or deform the frame of the container.

Referring again to FIG. 6D, the desired pressurization of the chamber 17 may be achieved by proper design of the plunger 22, channel 28, and pressure control grooves 42 and by use of the equation:

$$P_1 * V_1 = P_2 * V_2;$$

where:

$P_1$ is equal to the pressure in the container 12 prior to insertion of the plunger 22;

$V_1$ is equal to the volume of the channel 28 between the surface level S and the depth $D_1$ to which the grooves 42 extend;

$P_2$ is equal to the desired final pressure in the chamber 17 after insertion of the plunger 22 into the channel 28; and $V_2$ is equal to the volume of the channel 28 between the surface level S and the depth $D_2$ at which the piston 32 establishes a seal with the walls of the channel 28 when the plunger 22 is fully inserted into the channel.

To ensure the desired pressurization $P_2$ of the chamber 17, one should size the channel 28 and pressure stroke distance $D_3$ such that the ratio of the volumes $V_1:V_2$ is equal to the ratio of the pressures $P_2:P_1$. An engineer having ordinary skill in the art will be able to select suitable values for the volumes $V_1$ and $V_2$ using the description and equation given above. For example, in the presently preferred embodiment, the initial pressure $P_1$ in the container is equal to standard atmospheric pressure of about 14.7 psi, the volume $V_1$ is equal to 110 µl, the depth $D_1$ is equal to 0.2 inches, the depth $D_2$ is equal to 0.28 inches to give a pressure stroke distance $D_3$ of 0.08 inches, and the volume $V_2$ is equal to 60 µl to give a final pressure $P_2$ of about 26.7 psi (the desired 12 psi above ambient pressure). This is just one example of suitable dimensions for the container 12 and is not intended to limit the scope of the invention. Many other suitable values may be selected.

In selecting suitable dimensions for the channel 28 and pressure stroke distance $D_3$ (and thus the volumes $V_1$, $V_2$), there is no theoretical limit to how large or small the dimensions may be. It is only important that the ratio of the volumes $V_1:V_2$ yield the desired final desired pressure P2 in the chamber. As a practical matter, however, it is presently preferred to design the container such that the distance D3 of the pressure stroke is at least 0.05 inches, i.e., so that the plunger 22 when fully inserted into the channel 28 extends to a depth $D_2$ that is at least 0.05 inches below the depth $D_1$ at which the pressure control grooves end. This minimum length of the pressure stroke is preferred to reduce or make negligible the effect that any manufacturing or operating errors may have on the pressurization of the chamber. For example, the length of the pressure stroke may differ slightly from container to container due to manufacturing deviations, or the volume of air compressed may vary due to operator error in filling the container (e.g., different fill levels). If the container is designed to have a sufficiently long pressure stroke, however, such variances will have a lesser or negligible effect on the ratio of volumes $V_1:V_2$ and suitable pressurization of the chamber will still occur.

The pressure control grooves 42 provide several important advantages. First, the grooves 42 provide a simple mechanism for precisely and accurately controlling the pressure stroke of the plunger 22, and hence the pressurization of the chamber 17. Second, the grooves 42 allow the plunger 22 to become fully aligned with the channel 28 before the pressure stroke begins and thus prevent the plunger from becoming misaligned or cocked in the channel. This ensures a highly consistent pressure stroke. Although it is possible for the container to have only one pressure control groove, it is preferable for the container to have multiple grooves (e.g., 2 to 6 grooves) spaced equidistantly about the circumference of the channel 28. Referring again to FIG. 6A, the grooves 42 preferably cut about 0.01 to 0.03 inches into the surface 41 defining the channel 28. This range is preferred so that the grooves.42 are large enough to allow air to escape from the channel 28, but do not cut so deeply into the surface 41 that they degrade the structural integrity of the frame 16.

Although the grooves 42 are presently preferred, it is also possible to construct the container 12 without the grooves and still achieve pressurization of the chamber 17. In embodiments in which the container lacks pressure control grooves, the pressure stroke of the plunger 22 begins when the piston 32 enters the channel 28 and establishes a seal with the walls of the channel. In these embodiments, the volume $V_1$ (for use in the equation above) is equal to the volume of the channel 28 between the liquid surface level S and the port 14 where the piston 32 first establishes a seal with the walls of the channel.

Figure 3:
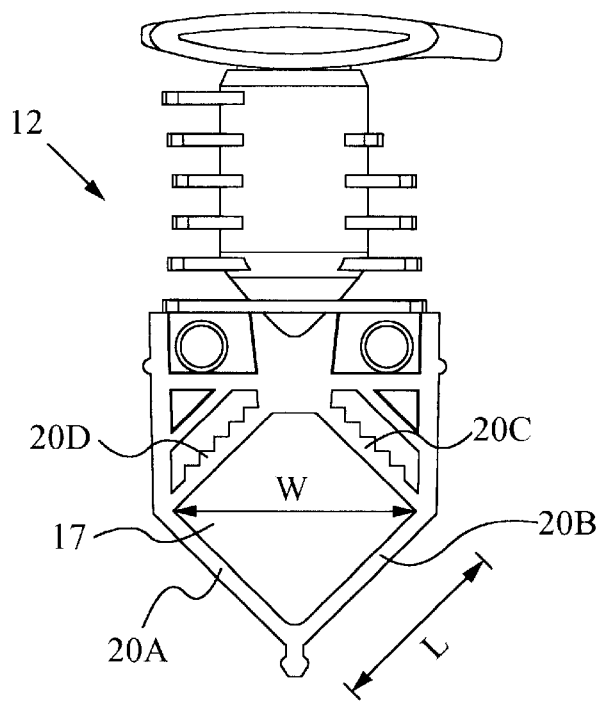
FIG. 3 is another schematic, front view of the container of FIG. 1.
Figure 4:
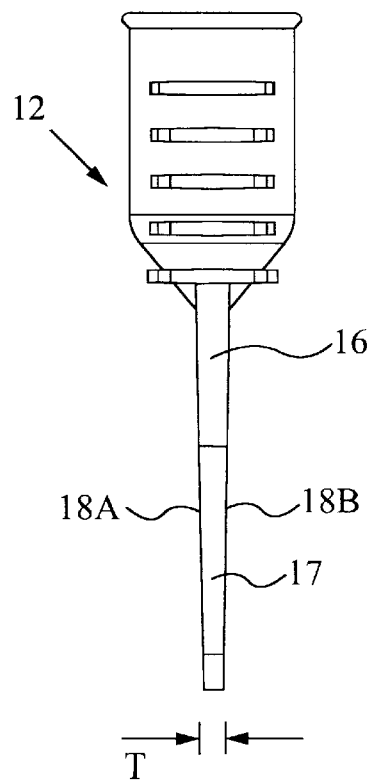
FIG. 4 is a side view of the container of FIG. 1.
Figure 5:
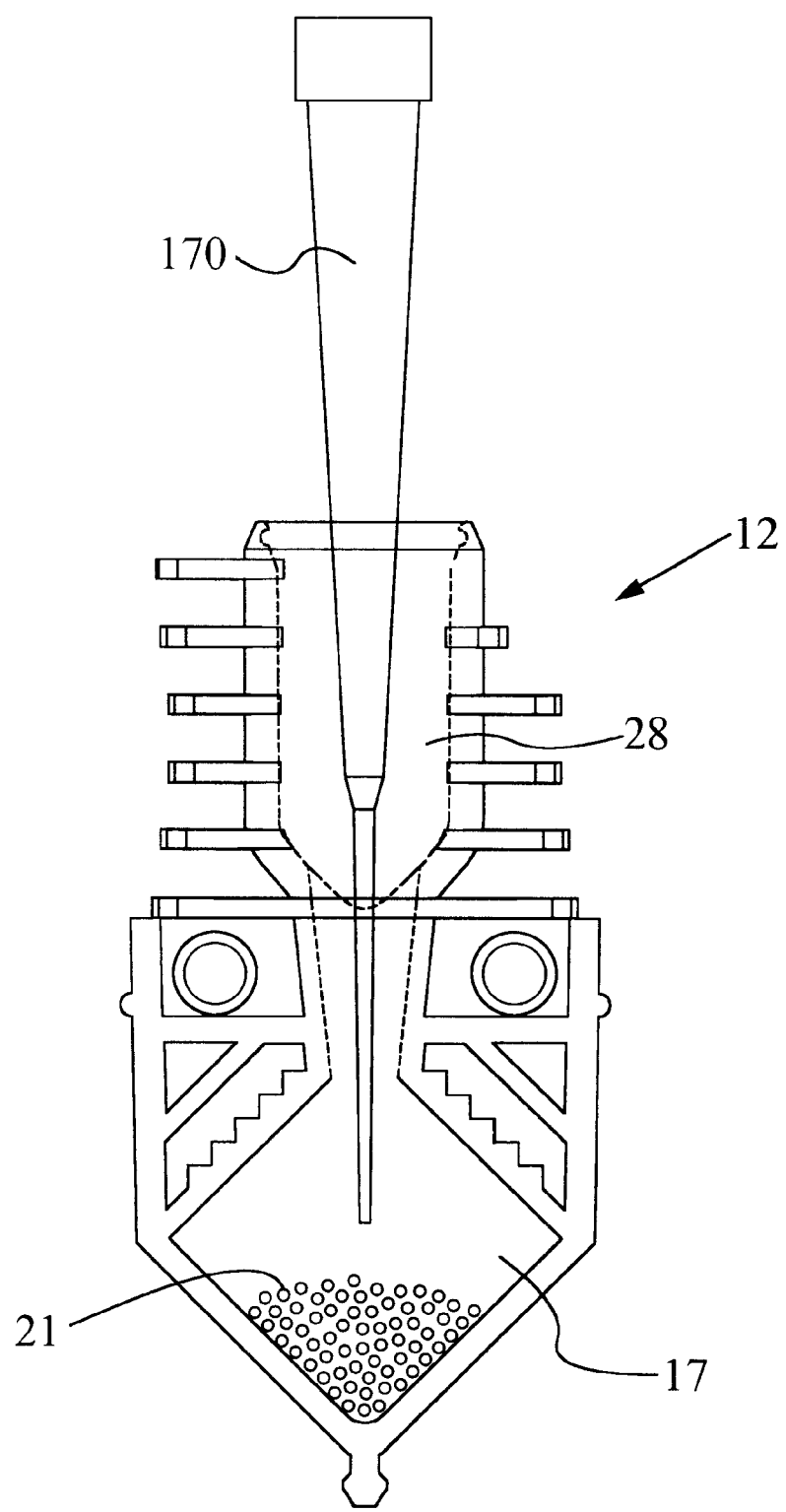
FIG. 5 is another schematic, front view of the container of FIG. 1 with a pipette tip inserted into the container.

A preferred method for disrupting cells or viruses according to the present invention will now be described with reference to FIGS. 1–12. Referring to FIG. 5, beads 21 are placed in the chamber 17 of the container to enhance the disruption of the cells or viruses. In general, the beads 21, may be composed of glass, plastic, polystyrene, latex, crystals, metals, metal oxides, or non-glass silicates. The beads 21 may be porous or non-porous and preferably have a diameter in the range of 1 to 200 $\mu$m. More preferably, the beads 21 are either borosilicate glass beads or soda lime glass beads having an average diameter of about 106 $\mu$m. Such beads have produced good results in experimental testing.

The beads 21 may be placed in the chamber 17 using a funnel. The funnel should be sufficiently long to extend from the port 14 through the channel 28 and into the chamber 17. After inserting the funnel into the container 12, the beads 21 are placed in the funnel and the container 12 is tapped lightly (e.g., against a bench top) until the beads 21 settle into the bottom of the chamber 17. It is preferred that the funnel extend through the channel 28 and into the chamber 17 as the beads 21 are added to the chamber to prevent the beads from contaminating the channel. The presence of beads in the channel 28 would interfere with the subsequent stroke of the plunger into the channel. The quantity of beads 21 added to the chamber 17 is preferably sufficient to fill about 10% to 40% of the volume capacity of the chamber. For example, in the presently preferred embodiment, the chamber 17 has a volume capacity of about 100 $\mu$l, and 30 to 40 mg of beads are placed into the chamber. The beads 21 may be placed in the chamber 17 just prior to the use of the container 12. Alternatively, the beads 21 may be placed in the chamber 17 during the manufacture of the container.

After the beads 21 are placed in the chamber 17, the chamber is filled with a liquid or gel containing the cells or viruses to be disrupted. The chamber 17 may be filled using a pipette having a pipette tip 170 (e.g., a standard 200 p$\mu$l loading tip). Alternatively, the chamber 17 may be filled using a syringe or any other suitable injection system. The liquid or gel should be a medium through which ultrasonic energy can be transmitted. For example, the liquid or gel may comprise deionized water or ultrasonic gel for holding the cells or viruses in suspension or solution. Alternatively, the liquid or gel may comprise a biological sample containing the cells or viruses. Suitable samples include bodily fluids (e.g., blood, urine, saliva, sputum, seminal fluid, spinal fluid, mucus, etc) or environmental samples such as ground or waste water. The sample may be in raw form or mixed with diluents or buffers. The liquid or gel may also include one or more lysing agents to aid in the disruption of the cells or viruses. One of the advantages of the present invention, however, is that harsh lysing agents are not required for successful disruption of the cells or viruses.

As shown in FIG. 6A, the container 12 is filled with the liquid or gel to the surface level S. As shown in FIG. 6D, the plunger 12 is then inserted into the channel 28 to seal and pressurize the container 12. As the plunger 22 is inserted, the piston 32 compresses gas in the channel 28 to increase pressure in the chamber 17, preferably to about 8 to 15 psi above ambient pressure, as previously described.

Referring to FIG. 12, the holder 60 is then pushed or pulled away from the horn tip 84 (in the direction of the rod 92) so that the container 12 can be inserted into the holder. The container 12 is then placed in the holder 60. During the insertion of the container 12, the holder 60 should be held a sufficient distance from the retaining pins 86 to provide clearance between the pins 86 and the tab 27. After the container 12 is inserted into the holder 60, the holder is gently released and the spring 90 pushes the holder 60 along the guide 62 until the wall 18A contacts and conforms to the surface of the horn tip 84. When the wall 18A is coupled to the horn tip 84, the spring 90 applies to the holder 60, and thus to the container 12, a substantially constant force to press the wall 18A against the horn tip 84. The force provided by the spring 90 ensures effective coupling between the wall 18A and horn tip 84 as ultrasonic energy is transmitted to the chamber 17. The horn tip 84 may optionally be coated with a fluid or gel prior to being placed in contact with the wall 18A to improve the coupling between the wall 18A and the horn tip 84. As shown in FIG. 11, when the container 12 is moved into contact with the horn tip 84, the tab 27 slides between the retaining pins 86. The pins 86 prevent the container from sliding upward in response to the motion of the horn tip 84.

Referring again to FIG. 12, the cells or viruses in the chamber 17 are then disrupted by transmitting ultrasonic energy from the horn 58 into the chamber 17 through the wall 18A. The magnitude of the force provided by the spring 90 to press together the wall 18A and the horn tip 84 is important for achieving a consistent transfer of energy between the horn and the chamber. If the force is too light, the wall 18A will only be held lightly against the horn tip 84, leading to intermittent contact between the horn tip 84 and the wall 18A and poor control over the transfer of ultrasonic energy into the chamber 17. If the force is too strong, the container 12 or wall 18A may be damaged during sonication. An intermediate force results in the most consistent and repeatable transfer of ultrasonic energy from the horn 58 to the chamber 17. It is presently preferred that the spring 90 provide a force in the range of 0.25 to 4 lbs., with a force of about 1 lb. being the most preferred. Forces in this range provide good coupling between the horn tip 84 and the wall 18A without leading to damage of the wall 18A.

When the horn 58 is activated, the horn tip 84 vibrates to transmit ultrasonic energy into the chamber 17. There is a relationship between the coupling force between the wall 18A and the horn tip 84 and the desired amplitude of the vibratory movements of the horn tip 84. A balance can be sought between the coupling force and the amplitude. Generally, a light coupling force requires a greater amplitude to effect disruption of the cells or viruses, while a stronger coupling force requires less amplitude to effect disruption. For the range of coupling forces presently preferred (0.25 to 4 lbs.), the amplitude of the vibratory movements should be in the range of 2 to 20 µm, with a preferred amplitude of amount 7.5 Mm. This range of amplitudes corresponds to a power output of about 2 to 20 W, with a preferred power output of about 5 W. As used herein, the term "amplitude" refers to the extent of a vibratory movement of the horn tip 84 measured from the mean position of the tip to an extreme position of the tip.

The ultrasound is preferably transmitted at a frequency in the range of 20 to 50 kHz, with a frequency of about 40 kHz being preferred. The duration of time for which ultrasonic energy is transmitted to the chamber is preferably in the range of 5 to 30 seconds. This range is preferred because it usually takes at least 5 seconds to disrupt the cells or viruses in the chamber, while sonicating the chamber for longer than 30 seconds will most likely denature or shear the nucleic acid released from the disrupted cells or viruses. Extensive shearing of the nucleic acid could interfere with subsequent amplification or detection. More preferably, the ultrasonic energy is transmitted to the chamber for about 10–20 seconds to fall safely within the practical limits stated above. The optimal time that a particular type of cell sample should be subjected to ultrasonic energy may be determined empirically.

The transmission of ultrasonic energy into the chamber 17 rapidly and consistently disrupts the cells or viruses to release the nucleic acid therefrom. While the precise interaction between the cells and the ultrasonic waves is not known and the applicants do not wish to be bound or limited by any theory, it is believed that the ultrasonic waves cause cavitation (the making and breaking of microscopic bubbles) in the liquid containing the cells. As these bubbles or cavities grow to resonant size, they collapse violently, producing very high local pressure changes. The pressure changes provide a mechanical shock to the cells or viruses, resulting in their disruption. The disruption of the cells or viruses may also be caused by sharp pressure rises resulting from the horn tip repeatedly hitting the wall of the chamber.

It is also believed that the beads in the chamber enhance the disruption of the cells or viruses in at least one of two ways. First, it is believed that the beads enhance cavitation by providing more surface area for the formation of the bubbles, resulting in a greater number of high pressure pockets being formed in the liquid. Second, the beads themselves may mechanically rupture the cells or viruses, i.e. ballistic disruption. The beads should be sufficiently small (e.g., 200 µm or less in diameter) so that they move throughout the volume of liquid in the chamber when the chamber is subjected to ultrasonic energy. In experimental testing, the applicants have found that it is usually necessary to use beads in combination with ultrasonic energy to disrupt certain types of cells (particularly spores) having highly resistant cell walls. Other types of cells, such as blood cells, are easier to disrupt and may often be disrupted without the use of beads.

Following disruption of the cells or viruses, the container 12 is removed from the holder 60 by pulling the holder 60 away from the horn tip 84 and withdrawing the container from the holder. The liquid or gel containing the disrupted cells and released nucleic acid is then removed from the container 12. This may be accomplished by centrifuging the container 12 and removing the supernatant using, e.g., a pipette or syringe. Alternatively, the liquid may be removed from the container 12 by setting the container on edge and at an incline until the beads precipitate. The beads usually settle in about 15 to 20 seconds. When the beads have settled, the plunger is withdrawn from the container 12 and the liquid is removed using a syringe or pipette. The released nucleic acid contained in the liquid may then be amplified and detected using techniques well known in the art.

One advantage of the apparatus and method of the present invention is that it provides for the rapid and effective disruption of cells or viruses, including tough spores, without requiring the use of harsh chemicals. In addition, the apparatus and method provide for highly consistent and repeatable lysis of cells or viruses, so that consistent results are achieved from one use of the apparatus to the next. The amount of ultrasonic energy that is absorbed by the liquid and beads held in the chamber 17 depends on the amplitude of the oscillations of the horn tip 84, the mass of the contents of the chamber 17, the pressure in the chamber 17, and the coupling force between the horn tip 84 and the wall 18A. All four of these parameters should be held substantially constant from one use of the apparatus to the next in order to achieve the same amount of ultrasonic action repeatably.

Many different modifications to the apparatus shown in FIG. 12 are possible. For example, the holder 60 may be slidably mounted to the base 54 by a variety of means, including rails, wheels, sliding in a groove, sliding in a cylinder, etc. Alternatively, the holder 60 may be fixedly attached to the base 54 and the horn 58 slidably mounted to the base. In this embodiment, an elastic body is positioned to apply a force to the horn 58 (either directly or to a holder holding the horn) to press together the horn tip 84 and the wall 18A. In addition, in each of these embodiments, the elastic body may be positioned to either push or pull the horn 58 or the container 12 towards each other. For example, the spring 90 may be positioned to push or pull the holder 60 towards the horn tip 84 or to push or pull the horn 58 towards the holder 60. Further, multiple elastic bodies may be employed to apply forces to both the container 12 and the horn 58 to push or pull them towards each other. All of these embodiments are intended to fall within the scope of the present invention.

Although a coil spring 90 is shown in FIG. 12, it is to be understood that any type of elastic body may be used in the apparatus and method of the invention to press together the wall 18A and the horn tip 84. Suitable elastic bodies include, but are not limited to, coil springs, wave springs, torsion springs, spiral springs, leaf spring, elliptic springs, half-elliptic springs, rubber springs, and atmospheric springs. The elastic body may also be compressed air or rubber. Preferably, the elastic body is a coil spring. Coil springs are preferred because they are simple and inexpensive to place in the apparatus and because the have a low spring rate. A compressed air system is also effective, but considerably more expensive. In embodiments in which the elastic body is a spring, the spring should have a low spring rate, preferably less than 4 lb/in. A low spring rate minimizes the effect that any variations in the thickness of the chamber 17 (due to small variations in manufacturing, filling, or pressurizing the container) will have on the magnitude of the force provided by the spring to press together the wall 18A and the horn tip 84.

The horn 58 is preferably a titanium horn having an integral piezoelectric driver to generate the energy necessary for disruption of the cells or viruses. Suitable horns are commercially available from Sonics & Materials, Inc. having an office at 53 Church Hill, Newton, Conn. 06470-1614 USA. In alternative embodiments, the ultrasonic transducer may comprise a piezoelectric disk or any other type of ultrasonic transducer that may be coupled to the container. It is presently preferred to use an ultrasonic horn because the horn structure is highly resonant and provides for repeatable and sharp frequency of excitation and large motion of the horn tip.

Another advantage of the apparatus and method of the present invention is that the chamber 17 of the container holds the cells or viruses in a thin volume of liquid that can be uniformly sonicated easily. Referring to FIGS. 3–4, it is presently preferred to construct the container 12 such that each of the sides walls 20A, 20B, 20C, 20D of the chamber has a length L in the range of 5 to 20 mm, the chamber has a width W in the range of 7 to 30 mm, and the chamber has a thickness T in the range of 0.5 to 5 mm. In addition, the chamber 17 preferably has a width W greater than its thickness T. In particular, the ratio of the width W of the chamber to the thickness T of the chamber is preferably at least 2:1. More preferably, the ratio of the width W of the chamber to the thickness T of the chamber is at least 4:1. These ratios are preferred to enable the entire volume of the chamber 17 to be rapidly and uniformly sonicated. In general, the volume capacity of the chamber 17 is preferably in the range of 0.02 to 1 ml.

Referring again to FIG. 12, the thickness of the chamber 17 (and thus the spacing between the walls 18A and 18B) is preferably less than half of the diameter of the horn tip 84. This relationship between the thickness of the chamber 17 and the diameter of the horn tip 84 ensures that the ultrasonic energy received from the horn 58 is substantially uniform throughout the volume of the chamber 17. As a specific example, in the presently preferred embodiment, the horn tip 84 has a diameter of 6.35 mm and the chamber 17 has a thickness of about 1.0 mm. In addition, the major wall 18A should be slightly larger than the surface of the horn tip 84 that presses against the wall 18A. This allows the flexible wall 18A to flex in response to the vibratory motion of the horn tip 84.

A preferred method for fabricating the container 12 will now be described with reference to FIGS. 1–2. The container 12 may be fabricated by first molding the rigid frame 16 using known injection molding techniques. The frame 16 is preferably molded as a single piece of polymeric material, e.g., polypropylene or polycarbonate. After the frame 16 is produced, thin, flexible sheets are cut to size and sealed to opposite sides of the frame 16 to form the major walls 18A, 18B of the chamber 17.

The major walls 18A, 18B are preferably cast or extruded films of polymeric material, e.g., polypropylene films, that are cut to size and attached to the frame 16 using the following procedure. A first piece of film is placed over one side of the bottom portion of the frame 16. The frame 16 preferably includes a tack bar 47 for aligning the top edge of the film. The film is placed over the bottom portion of the frame 16 such that the top edge of the film is aligned with the tack bar 47 and such that the film completely covers the bottom portion of the frame 16 below the tack bar 47. The film should be larger than the bottom portion of the frame 16 so that it may be easily held and stretched flat across the frame. The film is then cut to size to match the outline of the frame by clamping to the frame the portion of the film that covers the frame and cutting away the portions of the film that extend past the perimeter of the frame using, e.g., a laser or die. The film is then tack welded to the frame, preferably using a laser.

The film is then sealed to the frame 16, preferably by heat sealing. Heat sealing is presently preferred because it produces a strong seal without introducing potential contaminants to the container as the use of adhesive or solvent bonding techniques might do. Heat sealing is also simple and inexpensive. At a minimum, the film should be completely sealed to the surfaces of the side walls 20A, 20B, 20C, 20D. More preferably, the film is additionally sealed to the surfaces of the support ribs 15 and tack bar 47. The heat sealing may be performed using, e.g., a heated platen. An identical procedure may be used to cut and seal a second sheet to the opposite side of the frame 16 to complete the chamber 17.

Although two flexible sheets are preferred, the reaction container may have only one flexible sheet forming a major wall of the chamber. In this embodiment, the rigid frame defines the other major wall of the chamber, as well as the side walls of the chamber. The major wall formed by the frame should have a minimum thickness of about 1.25 mm (the practical minimum thickness for injection molding). The advantage to this embodiment is that the manufacturing of the container is simplified, and hence less expensive, since only one flexible sheet need be attached to the frame. The disadvantage is that the ultrasonic action in the chamber may be less than if both major walls are formed by flexible sheets.

The plunger 22 is also preferably molded from polymeric material (e.g., polypropylene or polycarbonate) using known injection molding techniques. As shown in FIG. 1, the frame 16, plunger 22, and leash 24 connecting the plunger to the frame may all be formed in the same mold to form a one-piece part. This embodiment of the container is especially suitable for manual use in which a human operator fills the container and inserts the plunger 22 into the channel 28. The leash 24 ensures that the plunger 22 is not lost or dropped on the floor. Alternatively, as shown in FIG. 2, the plunger 22 may be molded separately from the frame 16 so that the plunger and frame are separate pieces. This embodiment is especially suitable for automated use of the container in which the plunger 22 is picked and placed into the channel 28 by an automated machine.

The plunger 22 is presently preferred as a simple, effective, and inexpensive mechanism for increasing pressure in the chamber 17 and for sealing the chamber 17 from the external environment. It is to be understood, however, that the scope of the invention is not limited to this embodiment. There are many other suitable techniques for sealing and pressurizing the container. For example, in one alternative embodiment, the container has a cap for sealing the port 14 and the cap has a one-way valve through which fluid may be injected into the container. After the chamber of the container is filled, the cap is placed on the container and gas (e.g., air) from a pressure source is injected through the valve to pressurize the chamber. In another embodiment, a self-sealing, elastomeric plug is inserted into the channel 28 to seal the chamber 17. A needle is then inserted through the plug to inject air into the container to increase the pressure in the chamber. When the needle is removed from the plug, the plug self-seals so that the pressure in the chamber is maintained. In addition, any suitable pressure source may be used to pressurize the chamber. Suitable pressure sources include syringe pumps, compressed air sources, pneumatic pumps, or connections to external sources of pressure.

Although it is presently preferred to pressurize the chamber 17 prior to coupling the chamber to the ultrasonic transducer, it is to be understood that the pressure in the chamber 17 may simply be equal to the ambient pressure surrounding the container 12 (e.g., atmospheric pressure). If the port 14 is sealed, ambient pressure in the chamber 17 will still provide for sufficient conformity between the wall 18A and the surface of the transducer. The port 14 may be sealed using any suitable closure mechanism such as a screw cap, snap-on cap, heat seal, etc.

SUMMARY, RAMIFICATIONS, AND SCOPE

Although the above description contains many specificities, these should not be construed as limitations on the scope of the invention, but merely as examples of some of the presently preferred embodiments. Many modifications or substitutions may be made to the apparatus and methods described without departing from the scope of the invention. For example, the container for holding the cells or viruses need not be the specialized container described in the preferred embodiment above. Any type of container having a chamber for holding the cells or viruses may be used to practice the invention. Suitable containers include, but are not limited to, reaction vessels, cuvettes, cassettes, and cartridges. The container may have multiple chambers and/or channels for performing multiple. sample preparation functions, or the container may have only a single chamber for holding cells or viruses for disruption. In addition, the ultrasonic transducer for transmitting ultrasonic energy into the container may be an ultrasonic horn, piezoelectric disk, or any other type of ultrasonic transducer.

Further, the support structure for pressing the ultrasonic transducer and the container against each other may have many alternative forms. For example, in one alternative embodiment, the support structure includes a vise or clamp for pressing the transducer and container against each other. In another embodiment, the apparatus includes a pressure system for applying air pressure to press together the transducer and the container. Alternatively, magnetic or gravitational force may be used to press together the transducer and the container. In each embodiment of the invention, force may be applied to the transducer, to the container, or to both the transducer and the container.

Therefore, the scope of the invention should be determined by the following claims and their legal equivalents.

What is claimed is:

1. An apparatus for disrupting cells or viruses, the apparatus comprising:
   a) a container having a chamber for holding the cells or viruses, wherein the container includes at least one wall defining the chamber;
   b) an ultrasonic transducer for contacting an external surface of the wall and for transmitting ultrasonic energy into the chamber through the wall; and
   c) a support structure for holding the container and the transducer against each other such that the transducer contacts the external surface of the wall and for applying to the container or to the transducer a substantially constant force to press together the transducer and the wall.

2. The apparatus of claim 1, wherein the support structure comprises:
   a) a base;
   b) a first holder attached to the base for holding the transducer;
   c) a second holder slidably mounted to the base for holding the container and for positioning the container against the transducer such that the external surface of the wall contacts the transducer; and
   d) at least one elastic body for applying to the second holder the substantially constant force to press the wall against the transducer.

3. The apparatus of claim 2, wherein the elastic body comprises a spring, and wherein the apparatus further comprises means for adjusting the preload on the spring.

4. The apparatus of claim 1, wherein the chamber is defined by:
   a) a first wall for contacting the transducer, wherein the first wall is sufficiently flexible to conform to a surface of the transducer;
   b) a second wall spaced apart from the first wall, wherein the second wall is sufficiently flexible to move inwardly or outwardly as ultrasonic energy is received in the chamber; and
   c) a rigid frame defining the side walls of the chamber, wherein the side walls connect the flexible walls to each other;
   d) and wherein the support structure includes a holder for holding the frame such that the flexible walls are substantially unrestrained by the holder.

5. The apparatus of claim 4, wherein the holder comprises a body having a recess for receiving the frame and having an opening adjacent the recess, the opening being positioned to permit the outward expansion of the second wall when the container is positioned in the recess.

6. The apparatus of claim 4, wherein each of the flexible walls comprises a film of polymeric material, and wherein each of the flexible walls has a thickness in the range 0.025 to 0.1 mm.

7. The apparatus of claim 4, wherein the spacing between the first and second flexible walls is less than or equal to 5 mm.

8. The apparatus of claim 1, wherein the transducer comprises an ultrasonic horn having a tip for contacting the wall, and wherein the thickness of the chamber is less than or equal to half of the diameter of the tip.

9. The apparatus of claim 1, wherein the transducer comprises an ultrasonic horn having a tip for contacting the wall, and wherein the wall is sufficiently flexible to conform to a surface of the tip.

10. The apparatus of claim 9, wherein the container includes a port and a channel connecting the port to the chamber, and wherein the apparatus further comprises a plunger that is inserted into the channel to increase pressure in the chamber.

11. The apparatus of claim 10, wherein the plunger has a pressure stroke sufficient to increase the pressure in the chamber to at least 2 psi above the ambient pressure external to the container.

12. The apparatus of claim 10, wherein the plunger has a pressure stroke sufficient to increase the pressure in the chamber to at least 8 psi above the ambient pressure external to the container.

13. The apparatus of claim 1, wherein the wall comprises a film of polymeric material, and wherein the wall has a thickness in the range 0.025 to 0.1 mm.

14. The apparatus of claim 1, wherein the force is in the range of 0.25 to 4 lbs.

15. The apparatus of claim 1, wherein the force is at least 1 lb.

16. The apparatus of claim 1, further comprising beads in the chamber.

17. The apparatus of claim 1, wherein the ratio of the width of the chamber to the thickness of the chamber is at least 2:1.

18. The apparatus of claim 17, wherein the ratio of the width of the chamber to the thickness of the chamber is at least 4:1.

19. The apparatus of claim 17, wherein the thickness of the chamber is less than 5 mm.

20. The apparatus of claim 1, further comprising means for increasing the pressure in the chamber to at least 2 psi above the ambient pressure external to the container.

21. The apparatus of claim 1, further comprising means for increasing the pressure in the chamber to at least 8 psi above the ambient pressure external to the container.

22. The apparatus of claim 1, wherein the support structure includes a spring for applying the force, and wherein the force is in the range of 0.25 to 4 lbs.

23. The apparatus of claim 1, wherein the support structure includes a spring for applying the force, and wherein the force is at least 1 lb.

24. The apparatus of claim 1, wherein the support structure includes a spring for applying the force, the spring having a spring rate less than 4 lbs/inch.

25. The apparatus of claim 1, wherein the support structure includes at least one elastic body for applying the force, the at least one elastic body being selected from the group consisting of a coil spring, wave spring, torsion spring, spiral spring, leaf spring, elliptic spring, and half-elliptic spring.

26. The apparatus of claim 1, wherein the transducer comprises an ultrasonic horn having a tip for contacting the wall.

27. The apparatus of claim 1, wherein the transducer comprises piezoelectric material.

28. An apparatus for holding a container for disrupting cells or viruses that are placed in a chamber of the container, the apparatus comprising:
   a) an ultrasonic transducer for transmitting ultrasonic energy to the chamber through a wall of the container; and
   b) a support structure for coupling the transducer to an external surface of the wall and for applying to the container or the transducer a substantially constant force to press together the transducer and the wall.

29. The apparatus of claim 28, further comprising beads in the chamber.

30. The apparatus of claim 28, wherein the support structure comprises:
   a) a base;
   b) a first holder attached to the base for holding the transducer;
   c) a second holder slidably mounted to the base for holding the container and for positioning the container against the transducer such that the wall contacts the transducer; and
   d) at least one elastic body for applying to the second holder the substantially constant force to press the wall against the transducer.

31. The apparatus of claim 28, wherein the transducer comprises an ultrasonic horn having a tip for contacting the wall.

32. The apparatus of claim 28, wherein the force is in the range of 0.25 to 4 lbs.

33. The apparatus of claim 28, wherein the force is at least 1 lb.

34. The apparatus of claim 28, wherein the support structure includes a spring for applying the force, and wherein the apparatus further comprises means for adjusting the preload on the spring.

35. The apparatus of claim 28, further comprising means for increasing the pressure in the chamber to at least 2 psi above the ambient pressure external to the container.

36. The apparatus of claim 28, further comprising means for increasing the pressure in the chamber to at least 8 psi above the ambient pressure external to the container.

37. The apparatus of claim 28, wherein the support structure includes a spring for applying the force, and wherein the force is in the range of 0.25 to 4 lbs.

38. The apparatus of claim 28, wherein the support structure includes a spring for applying the force, and wherein the force is at least 1 lb.

39. The apparatus of claim 28, wherein the support structure includes a spring for applying the force, the spring having a spring rate less than 4 lbs/inch.

40. The apparatus of claim 28, wherein the support structure includes at least one elastic body for applying the force, the at least one elastic body being selected from the group consisting of a coil spring, wave spring, torsion spring, spiral spring, leaf spring, elliptic spring, and half-elliptic spring.

41. The apparatus of claim 28, wherein the transducer comprises piezoelectric material.

42. A method for disrupting cells or viruses, the method comprising the steps of:
   a) holding a liquid or gel containing the cells or viruses in the chamber of a container;
   b) holding an ultrasonic transducer against a wall of the chamber;
   c) applying to the container or to the transducer a substantially constant force to press together the transducer and the wall; and
   d) transmitting ultrasonic energy from the transducer into the chamber.

43. The method of claim 42, further comprising the step of placing beads in the chamber prior to transmitting ultrasonic energy into the chamber.

44. The method of claim 42, wherein the ultrasonic energy is transmitted to the chamber for a duration of time less than 30 seconds.

45. The method of claim 42, wherein the transducer comprises an ultrasonic horn having a tip for contacting the wall of the chamber, and wherein the wall is sufficiently flexible to conform to the surface of the tip.

46. The method of claim 42, wherein the transducer comprises an ultrasonic horn having a tip for contacting the wall of the chamber, and wherein the thickness of the chamber is less than or equal to half of the diameter of the tip.

47. The method of claim 42, further comprising the step of pressurizing the chamber prior to transmitting ultrasonic energy into the chamber.

48. The method of claim 47, wherein the chamber is pressurized to at least 2 psi above the ambient pressure external to the container.

49. The method of claim 47, wherein the chamber is pressurized to at least 8 psi above the ambient pressure external to the container.

50. The method of claim 42, wherein the force is in the range of 0.25 to 4 lbs.

51. The method of claim 42, wherein the force is at least 1 lb.

52. The method of claim 42, wherein the force is applied by a spring having a spring rate less than 4 lbs/inch.

53. The method of claim 42, wherein the force is applied by at least one elastic body selected from the group consisting of a coil spring, wave spring, torsion spring, spiral spring, leaf spring, elliptic spring, and half-elliptic spring.

54. The method of claim 42, wherein the transducer comprises an ultrasonic horn having a tip that is held against the wall.

55. The method of claim 42, wherein the transducer comprises piezoelectric material.

56. A method for disrupting cells or viruses, the method comprising the steps of:
   a) providing a container having a chamber defined by:
      i) a first wall having an external surface for contacting an ultrasonic transducer, wherein the first wall is sufficiently flexible to conform to a surface of the transducer;
      ii) a second flexible wall spaced apart from the first wall; and iii) side walls connecting the flexible walls to each other, wherein the ratio of the width of the chamber to the thickness of the chamber is at least 2:1;

b) holding in the chamber:
   i) a liquid or gel containing the cells or viruses; and
   ii) beads;

c) placing the ultrasonic transducer in contact with the external surface of the first wall of the chamber; and d) transmitting ultrasonic energy from the transducer into the chamber.

57. The method of claim 56, further comprising the step of applying to the container or to the transducer a substantially constant force to press together the transducer and the first wall of the chamber.

58. The method of claim 57, wherein the force is applied by a spring having a spring rate less than 4 lbs/inch.

59. The method of claim 57, wherein the force is applied by at least one elastic body selected from the group consisting of a coil spring, wave spring, torsion spring, spiral spring, leaf spring, elliptic spring, and half-elliptic spring.

60. The method of claim 57, wherein the force is in the range of 0.25 to 4 lbs.

61. The method of claim 57, wherein the force is at least 1 lb.

62. The method of claim 56, wherein the transducer comprises an ultrasonic horn having a tip for contacting the first wall of the chamber, and wherein the thickness of the chamber is less than or equal to half of the diameter of the tip.

63. The method of claim 56, further comprising the step of pressurizing the chamber prior to transmitting ultrasonic energy into the chamber.

64. The method of claim 63, wherein the chamber is pressurized to at least 2 psi above the ambient pressure external to the container.

65. The method of claim 63, wherein the chamber is pressurized to at least 8 psi above the ambient pressure external to the container.

66. The method of claim 56, wherein the transducer comprises an ultrasonic horn having a tip that is placed in contact with the first wall.

67. The method of claim 56, wherein the transducer comprises piezoelectric material.

\* \* \* \* \*